(12) United States Patent
Batchelor et al.

(10) Patent No.: US 12,256,906 B2
(45) Date of Patent: Mar. 25, 2025

(54) MEDICAL DEVICES WITH BILIARY DIAGNOSTIC DEVICES

(71) Applicant: GYRUS ACMI, INC., Southborough, MA (US)

(72) Inventors: Kester Julian Batchelor, Mound, MN (US); Joey Magno, Dudley, MA (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 678 days.

(21) Appl. No.: 17/126,512

(22) Filed: Dec. 18, 2020

(65) Prior Publication Data
US 2021/0228146 A1 Jul. 29, 2021

Related U.S. Application Data

(60) Provisional application No. 63/037,098, filed on Jun. 10, 2020, provisional application No. 62/966,710, filed on Jan. 28, 2020.

(51) Int. Cl.
*A61B 1/273* (2006.01)
*A61B 1/00* (2006.01)
(Continued)

(52) U.S. Cl.
CPC .......... *A61B 1/273* (2013.01); *A61B 1/00097* (2022.02); *A61B 1/012* (2013.01);
(Continued)

(58) Field of Classification Search
CPC .................. A61F 2002/041; A61F 2/04; A61F 2230/0069; A61B 1/00097;
(Continued)

(56) References Cited

U.S. PATENT DOCUMENTS

| 4,690,152 A | 9/1987 | Juncosa |
| 5,178,620 A * | 1/1993 | Eggers ............... A61B 18/1492 606/41 |

(Continued)

FOREIGN PATENT DOCUMENTS

| JP | 2006518638 | 8/2006 |
| JP | 2008272478 | 11/2008 |

(Continued)

OTHER PUBLICATIONS

"International Application Serial No. PCT US2020 065897, International Search Report mailed Apr. 13, 2021", 6 pgs.
(Continued)

*Primary Examiner* — Benjamin S Melhus
*Assistant Examiner* — Severo Antonio P Lopez
(74) *Attorney, Agent, or Firm* — Schwegman Lundberg & Woessner, P.A.

(57) ABSTRACT

A biliary diagnostic device comprises a tubular body comprising an outer wall and an internal lumen, and a biliary diagnostic sensor comprising for analyzing biological matter in contact with the tubular body. A method of guiding an endoscope to a bile duct comprises inserting the endoscope into a duodenum, engaging a sensor with biological matter, electrically analyzing biological matter with the sensor to identify an electrical parameter, identifying liver bile in the biological matter from the electrical parameter, and guiding the endoscope through the duodenum based on the bile. A method of identifying biological matter comprises engaging a medical device sensor with biological matter in a bile duct, electrically analyzing biological matter with the sensor to identify an electrical parameter, identifying biological matter from a liver, pancreas or gall bladder from the electrical parameter, and outputting indicia of the biological matter to a user of the medical device.

25 Claims, 16 Drawing Sheets

(51) Int. Cl.
  *A61B 1/012*       (2006.01)
  *A61B 1/05*        (2006.01)
  *A61B 1/06*        (2006.01)
  *A61B 5/00*        (2006.01)
  *A61B 5/0538*      (2021.01)
  *A61B 18/00*       (2006.01)
  *A61B 18/08*       (2006.01)
  *A61B 34/20*       (2016.01)
  *A61F 2/04*        (2013.01)

(52) U.S. Cl.
  CPC .............. *A61B 1/05* (2013.01); *A61B 1/0655* (2022.02); *A61B 1/2736* (2013.01); *A61B 5/0538* (2013.01); *A61B 5/4244* (2013.01); *A61B 5/6862* (2013.01); *A61B 5/7405* (2013.01); *A61B 5/742* (2013.01); *A61B 18/082* (2013.01); *A61B 34/20* (2016.02); *A61F 2/04* (2013.01); *A61B 2018/00535* (2013.01); *A61B 2018/00595* (2013.01); *A61B 2034/2046* (2016.02); *A61B 2560/0223* (2013.01); *A61B 2562/085* (2013.01); *A61F 2002/041* (2013.01); *A61F 2230/0069* (2013.01)

(58) Field of Classification Search
  CPC ... A61B 1/00098; A61B 1/012; A61B 1/0125; A61B 1/05; A61B 1/0655; A61B 1/273; A61B 1/2736; A61B 5/0538; A61B 5/14503; A61B 5/14507; A61B 5/14546; A61B 5/4244; A61B 5/6852; A61B 5/6862; A61B 5/7405; A61B 5/742; A61B 18/082; A61B 34/20; A61B 2018/00535; A61B 2018/00595; A61B 2034/2046; A61B 2560/0223; A61B 2562/085
  See application file for complete search history.

(56) References Cited

U.S. PATENT DOCUMENTS

| | | | | |
|---|---|---|---|---|
| 5,517,989 | A * | 5/1996 | Frisbie | A61N 1/40 606/41 |
| H1905 | H * | 10/2000 | Hill | 607/122 |
| 6,346,014 | B1 * | 2/2002 | Griesser | H01R 13/5224 439/680 |
| 2004/0162586 | A1 * | 8/2004 | Covey | A61N 1/0472 607/5 |
| 2004/0172284 | A1 * | 9/2004 | Sullivan | G16H 40/67 705/2 |
| 2005/0245789 | A1 * | 11/2005 | Smith | A61B 1/0016 137/560 |
| 2006/0095030 | A1 * | 5/2006 | Avitall | A61M 25/0041 606/41 |
| 2006/0235269 | A1 | 10/2006 | Waxman | |
| 2007/0027385 | A1 * | 2/2007 | Brister | A61B 5/6848 600/347 |
| 2008/0167629 | A1 * | 7/2008 | Dann | A61M 25/0119 604/528 |
| 2009/0062684 | A1 | 3/2009 | Gregersen et al. | |
| 2010/0016699 | A1 * | 1/2010 | Wadhawan | A61B 5/14546 600/361 |
| 2010/0152607 | A1 * | 6/2010 | Kassab | A61B 5/1076 600/549 |
| 2011/0028816 | A1 * | 2/2011 | Simpson | A61B 5/14517 600/345 |
| 2011/0054381 | A1 | 3/2011 | Van et al. | |
| 2015/0025507 | A1 * | 1/2015 | Golden | A61M 25/0028 604/523 |
| 2019/0208997 | A1 * | 7/2019 | Rout | A61B 1/0646 |
| 2022/0241555 | A1 * | 8/2022 | Ghosheh | A61B 1/00097 |

FOREIGN PATENT DOCUMENTS

| | | |
|---|---|---|
| JP | 2009530051 | 8/2009 |
| JP | 2009537272 | 10/2009 |
| JP | 2013183792 | 9/2013 |
| JP | 2023511708 A | 3/2023 |
| WO | WO-2011140118 A1 | 11/2011 |
| WO | WO-2021154419 A1 | 8/2021 |

OTHER PUBLICATIONS

"International Application Serial No. PCT US2020 065897, Written Opinion mailed Apr. 13, 2021", 7 pgs.
"Chinese Application Serial No. 202080095067.1, Voluntary Amendment filed Dec. 28, 2022", with English translation of claims, 12 pgs.
"Indian Application Serial No. 202247041612, First Examination Report mailed Jan. 27, 2023", 6 pgs.
"Japanese Application Serial No. 2022-545939, Voluntary Amendment filed Jan. 30, 2023", with English translation of claims, 7 pgs.
"Chinese Application Serial No. 202080095067.1, Voluntary Amendment filed Dec. 28, 2022", w/ English Claims, 12 pgs.
"Japanese Application Serial No. 2022-545939, Notification of Reasons for Refusal mailed Aug. 22, 2023", w English Translation, 14 pgs.
"Indian Application Serial No. 202247041612, Response filed Aug. 18, 2023 to First Examination Report mailed Jan. 27, 2023", 30 pgs.
"German Application Serial No. 11 2020 006 126.4, Voluntary Amendment Filed Jul. 25, 2023", w/ english claims, 13 pgs.
"Japanese Application Serial No. 2022-545939, Final Notification of Reasons for Refusal mailed Mar. 12, 2024", w/ English translation, 8 pgs.
"Japanese Application Serial No. 2022-545939, Response filed Dec. 18, 2023 to Notification of Reasons for Refusal mailed Aug. 22, 2023", w/ english claims, 7 pgs.

* cited by examiner

MEDICAL DEVICES WITH BILIARY DIAGNOSTIC DEVICES

CROSS-REFERENCE TO RELATED PATENT DOCUMENTS

This patent application claims priority to U.S. Provisional Patent Application No. 63/037,098 filed Jun. 10, 2020 titled "Medical Devices With Biliary Diagnostic Devices" and also claims priority to U.S. Provisional Patent Application No. 62/966,710 filed on Jan. 28, 2020, titled, "Endoscope with a Biliary Diagnostic Device," the entire contents of which are hereby incorporated by reference.

TECHNICAL FIELD

The present disclosure relates generally to medical devices comprising elongate bodies configured to be inserted into incisions or openings in anatomy of a patient to provide diagnostic or treatment operations.

More specifically, the present disclosure relates to endoscopes for imaging and/or providing passage of therapeutic devices toward various anatomical portions, including gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like. The present application further relates to stents and other medical devices that can be used in gastrointestinal tract treatments and procedures.

BACKGROUND

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like.

In conventional endoscopy, the distal portion of the endoscope can be configured for supporting and orienting a therapeutic device, such as with the use of an elevator. In some systems, two endoscopes can be configured to work together with a first endoscope guiding a second endoscope inserted therein with the aid of the elevator. Such systems can be helpful in guiding small-diameter endoscopes to anatomic locations within the body that are difficult to reach. For example, some anatomic locations can only be accessed with an endoscope after insertion through a circuitous path. Furthermore, the tissue in some anatomic locations can be sensitive. As such, it can be undesirable to guide an endoscope to an unintended anatomic location.

SUMMARY

The present inventors have recognized that problems to be solved with conventional medical devices, and in particular endoscopes and duodenoscopes, include, among other things, 1) the difficulty in navigating endoscopes to difficult to reach anatomic locations, 2) the increased time and associated cost of navigating an endoscope to an incorrect location, and 3) the risk of potential tissue damage of impacting sensitive tissue with an endoscope. Such problems can be particularly present in duodenoscopy procedures (e.g., Endoscopic Retrograde Cholangio-Pancreatography, hereinafter "ERCP" procedures) where an auxiliary scope (also referred to as daughter scope, or cholangioscope) can be attached and advanced through the working channel of a "main scope" (also referred to as mother scope or duodenoscope). The present disclosure can help provide solutions to these and other problems by providing systems, devices and methods for sensing biological matter, e.g., biological fluids and solids, that can be used to diagnose medical conditions and guide insertion of medical devices to desired anatomic areas. In particular, the present application is directed biliary diagnostic devices that can evaluate biological fluid, e.g., liver bile, to guide endoscopes toward anatomical features where medical intervention is desired. For example, the presence of liver bile can facilitate guiding an endoscope toward a common bile duct and away from a main pancreatic duct from within a duodenum.

The present inventors have also recognized that problems to be solved with conventional medical procedures, and in particular duodenoscopy procedures, include, among other things, the potential desire to utilize fluoroscopy to facilitate navigation of complex anatomy. It can be desirable to avoid the use of fluoroscopy to minimize surgeon and patient exposure to radiation. The present disclosure can help provide solutions to these and other problems by providing systems, devices and methods utilizing non-fluoroscopy navigation assistance in the form of biliary diagnostic devices that can be used to perform biological or chemical analysis of anatomic matter to provide composition-guided navigation.

The present inventors have further recognized that problems to be solved with conventional treatment of stone, e.g., gallstone, formation in the gastrointestinal system is that diagnosing biological conditions that can lead to stone formation in a patient can be difficult. For example, often times the formation of the stones themselves provide the first indication of a medical condition. Additionally, procedures to remove the stone can result in the stone being destroyed. As such, it can be difficult to diagnose the specific conditions in the patient that led to the stone formation. The present disclosure can help provide solutions to these and other problems by providing systems, devices and methods that utilize biliary diagnostic devices to analyze the composition of gastrointestinal stones to thereby help identify biological conditions that led to the formation of the stone, to thereby provide the foundation for a treatments plan, such as a change in eating habits or pharmaceutical to reduce the risk of future recurrence of the issue.

In an example, a biliary diagnostic device can comprise a tubular body comprising an outer wall and an internal lumen, and a first biliary diagnostic sensor coupled to the medical device configured to analyze biological matter in contact with the tubular body.

In another example, a method of guiding an endoscope to a common bile duct from a duodenum can comprise inserting the endoscope into the duodenum, engaging a sensor of the endoscope with biological matter in the duodenum, electrically analyzing the biological matter with the sensor to identify an electrical parameter, identifying liver bile in the biological matter from the electrical parameter, and guiding the endoscope through the duodenum based on presence of the liver bile.

In an additional example, a method of identifying a composition of biological matter within a bile duct can comprise engaging a sensor of a medical device with biological matter in the bile duct, electrically analyzing the biological matter with the sensor to identify an electrical parameter, identifying biological matter from at least one of a liver, pancreas and a gall bladder in the biological matter from the electrical parameter, and outputting an indication of the biological matter to a user of the medical device.

DETAILED DESCRIPTION

Figure 1:
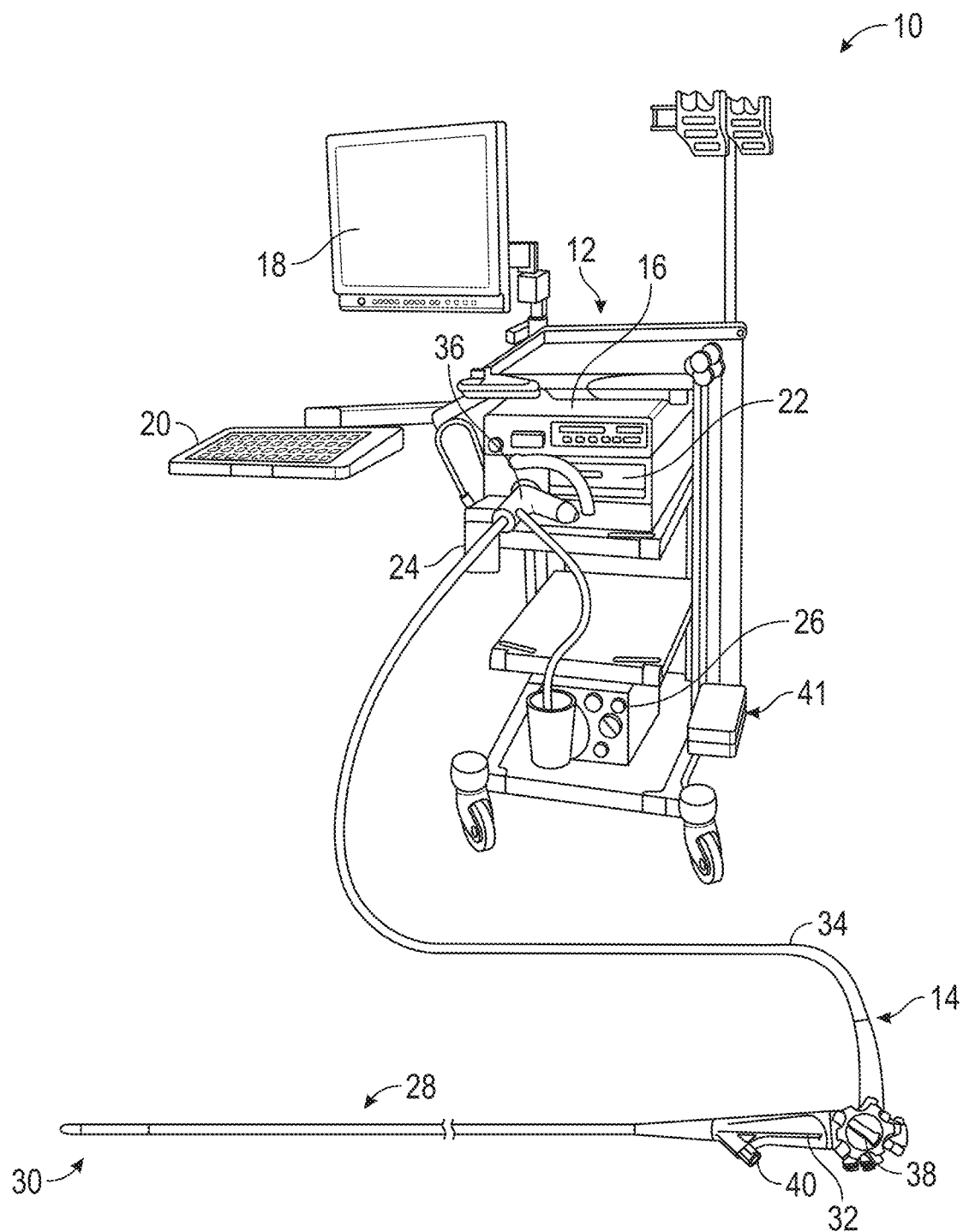
FIG. 1 is a schematic diagram of an endoscopy system comprising an imaging and control system and an endoscope, such as duodenoscope.

FIG. 1 is a schematic diagram of endoscopy system 10 comprising imaging and control system 12 and endoscope 14. The system of FIG. 1 is an illustrative example of an endoscopy system suitable for use with the systems, devices and methods described herein, such as biliary diagnostic devices that can be used for navigation assistance and analyzing of chemical compositions. According to some examples, endoscope 14 can be insertable into an anatomical region for imaging and/or to provide passage of one or more sampling devices for biopsies, or one or more therapeutic devices for treatment of a disease state associated with the anatomical region. Endoscope 14 can, in advantageous aspects, interface with and connect to imaging and control system 12. In the illustrated example, endoscope 14 comprises a duodenoscope, though other types of endoscopes can be used with the features and teachings of the present disclosure.

Imaging and control system 12 can comprise controller 16, output unit 18, input unit 20, light source 22, fluid source 24 and suction pump 26.

Imaging and control system 12 can include various ports for coupling with endoscopy system 10. For example, controller 16 can include a data input/output port for receiving data from and communicating data to endoscope 14. Light source 22 can include an output port for transmitting light to endoscope 14, such as via a fiber optic link. Fluid source 24 can include a port for transmitting fluid to endoscope 14. Fluid source 24 can comprise a pump and a tank of fluid or can be connected to an external tank, vessel or storage unit. Suction pump 26 can comprise a port used to draw a vacuum from endoscope 14 to generate suction, such as for withdrawing fluid from the anatomical region into which endoscope 14 is inserted. Output unit 18 and input unit 20 can be used by an operator of endoscopy system 10 to control functions of endoscopy system 10 and view output of endoscope 14. Controller 16 can additionally be used to generate signals or other outputs from treating the anatomical region into which endoscope 14 is inserted. In examples, controller 16 can generate electrical output, acoustic output, a fluid output and the like for treating the anatomical region with, for example, cauterizing, cutting, freezing and the like.

Endoscope 14 can comprise insertion section 28, functional section 30 and handle section 32, which can be coupled to cable section 34 and coupler section 36.

Insertion section 28 can extend distally from handle section 32 and cable section 34 can extend proximally from handle section 32. Insertion section 28 can be elongate and include a bending section, and a distal end to which functional section 30 can be attached. The bending section can be controllable (e.g., by control knob 38 on handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30. The working channel can extend between handle section 32 and functional section 30. Additional functionalities, such as fluid passages, guide wires, and pull wires can also be provided by insertion section 28 (e.g., via suction or irrigation passageways, and the like).

Handle section 32 can comprise knob 38 as well as ports 40. Knob 38 can be coupled to a pull wire extending through insertion section 28. Ports 40 can be configured to couple various electrical cables, fluid tubes and the like to handle section 32 for coupling with insertion section 28.

Imaging and control system 12, according to examples, can be provided on a mobile platform (e.g., cart 41) with shelves for housing light source 22, suction pump 26, image processing unit 42, etc. Alternatively, several components of imaging and control system 12 shown in FIGS. 1 and 2 can be provided directly on endoscope 14 so as to make the endoscope "self-contained."

Functional section 30 can comprise components for treating and diagnosing anatomy of a patient. Functional section 30 can comprise an imaging device, an illumination device and an elevator, as is described further with reference to FIGS. 3A-3C. Functional section 30 can further comprise a biliary diagnostic device as is described herein. For example, functional section 30 can comprise one or more electrodes conductively connected to handle section 32 and functionally connected to imaging and control system 12 to analyze biological matter in contact with the electrodes based on comparative biological data stored in imaging and control system 12.

Figure 2:
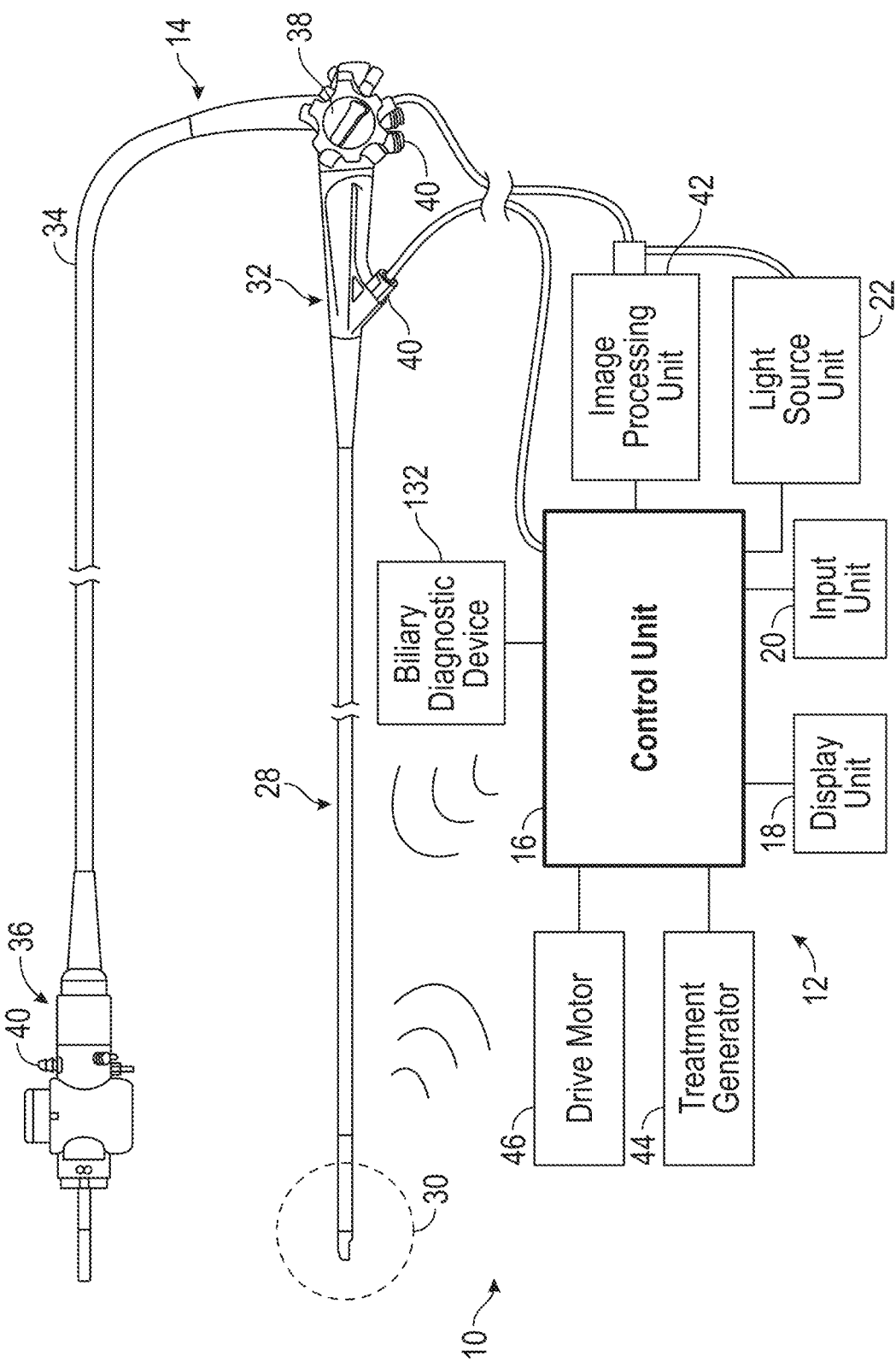
FIG. 2 is a schematic diagram of the endoscopy system of FIG. 1 comprising the endoscope connected to a control unit of the imaging and control system.

FIG. 2 is a schematic diagram of endoscopy system 10 of FIG. 1 comprising imaging and control system 12 and endoscope 14. FIG. 2 schematically illustrates components of imaging and control system 12 coupled to endoscope 14, which in the illustrated example comprises a duodenoscope. Imaging and control system 12 can comprise controller 16, which can include or be coupled to image processing unit 42, treatment generator 44 and drive unit 46, as well as light source 22, input unit 20 and output unit 18. As is discussed below in greater detail, controller 16 can comprise, or can be in communication with, biliary diagnostic device 132, which can comprise electrodes positioned on functional section 30 or insertion section 28.

Image processing unit 42 and light source 22 can each interface with endoscope 14 (e.g., at functional unit 30) by wired or wireless electrical connections. Imaging and control system 12 can accordingly illuminate an anatomical region, collect signals representing the anatomical region, process signals representing the anatomical region, and display images representing the anatomical region on display unit 18. Imaging and control system 12 can include light source 22 to illuminate the anatomical region using light of desired spectrum (e.g., broadband white light, narrow-band imaging using preferred electromagnetic wavelengths, and the like). Imaging and control system 12 can connect (e.g., via an endoscope connector) to endoscope 14 for signal transmission (e.g., light output from light source, video signals from imaging system in the distal end, diagnostic and sensor signals from a biliary diagnostic device, and the like).

Fluid source 24 can comprise one or more sources of air, saline or other fluids, as well as associated fluid pathways (e.g., air channels, irrigation channels, suction channels) and connectors (barb fittings, fluid seals, valves and the like).

Imaging and control system 12 can also include drive unit 46, which can be an optional component. Drive unit 46 can comprise a motorized drive for advancing a distal section of endoscope 14, as described in at least PCT Pub. No. WO 2011/140118 A1 to Frassica et al., titled "Rotate-to-Advance Catheterization System," which is hereby incorporated in its entirety by this reference.

Figure 3A:
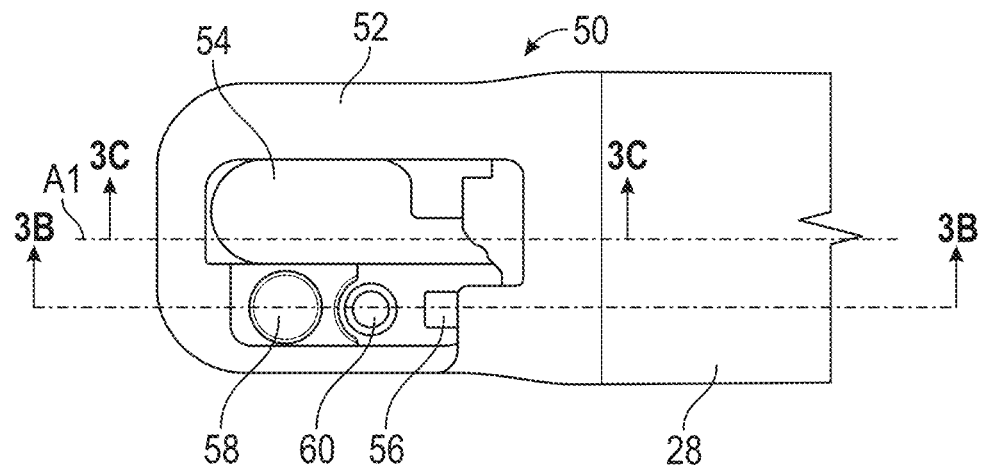
FIG. 3A is a schematic top view of a distal portion of the endoscope of FIG. 2 comprising a camera module including optical components for a side-viewing endoscope and an elevator mechanism.
Figure 3B:
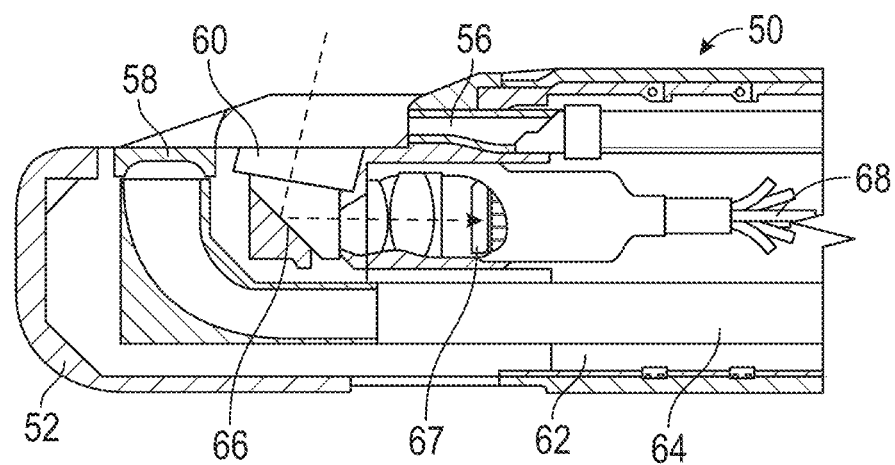
FIG. 3B is an enlarged cross-sectional view taken along the plane 3B-3B of FIG. 3A showing the optical components.
Figure 3C:
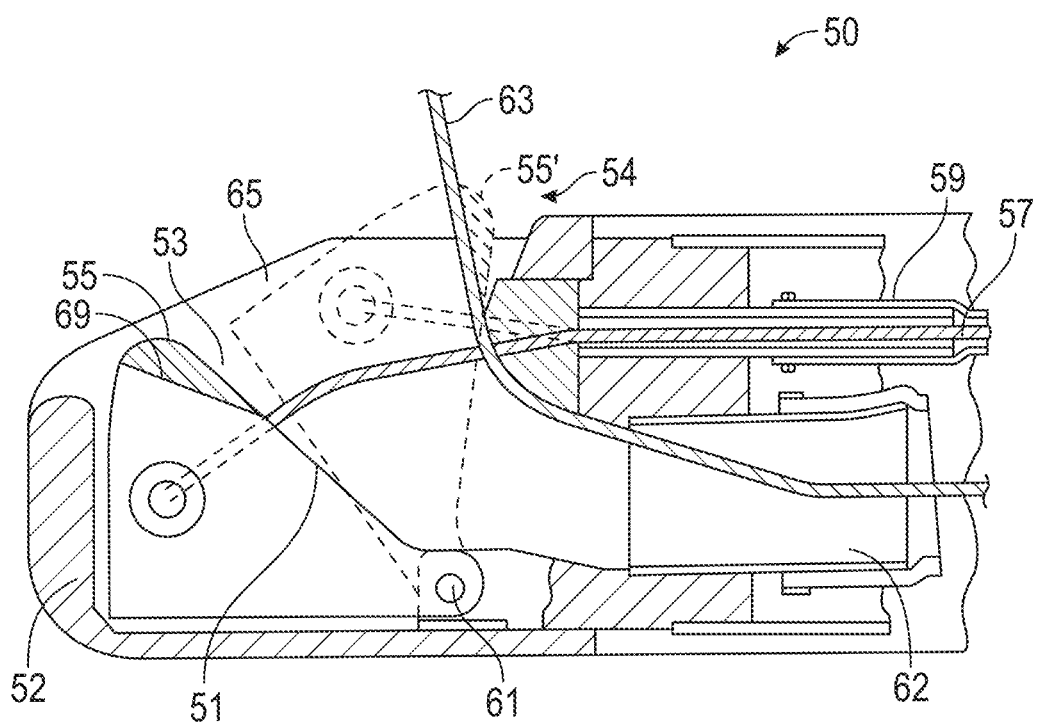
FIG. 3C is an enlarged cross-sectional view taken along the plane 3C-3C of FIG. 3A showing the elevator mechanism.

FIGS. 3A-3C illustrate a first example of functional section 30 of endoscope 14 of FIG. 2. FIG. 3A illustrates a top view of functional section 30 and FIG. 3B illustrates a cross-sectional view of functional section 30 taken along section plane 3B-3B of FIG. 3A. FIGS. 3A and 3B each illustrate "side-viewing endoscope" (e.g., duodenoscope) camera module 50. In side-viewing endoscope camera module 50, illumination and imaging systems are positioned such that the viewing angle of the imaging system corresponds to a target anatomy lateral to central longitudinal axis A1 of endoscope 14.

In the example of FIGS. 3A and 3B, side-viewing endoscope camera module 50 can comprise housing 52, elevator 54, fluid outlet 56, illumination lens 58 and objective lens 60. Housing 52 can form a fluid tight coupling with insertion section 28. Housing 52 can comprise opening for elevator 54. Elevator 54 can comprise a mechanism for moving a device inserted through insertion section 28. In particular, elevator 54 can comprise a device that can bend an elongate device extended through insertion section 28 along axis A1, as is discussed in greater detail with reference to FIG. 3C. Elevator 54 can be used to bend the elongate device at an angle to axis A1 to thereby treat the anatomical region adjacent side-viewing endoscope camera module 50. Elevator 54 is located alongside, e.g., radially outward of axis A1, illumination lens 58 and objective lens 60.

As can be seen in FIG. 3B, insertion section 28 can comprise central lumen 62 through which various components (e.g., electrode leads 162 and 166 (FIG. 5) of biliary diagnostic device 132) can be extended to connect functional section 30 with handle section 32 (FIG. 2). For example, illumination lens 58 can be connected to light transmitter 64, which can comprise a fiber optic cable or cable bundle extending to light source 22 (FIG. 1). Likewise, objective lens 60 can be coupled to prism 66 and imaging unit 67, which can be coupled to wiring 68. Also, fluid outlet 56 can be coupled to fluid line 69, which can comprise a tube extending to fluid source 24 (FIG. 1). Other elongate elements, e.g., tubes, wires, cables, can extend through lumen 62 to connect functional section 30 with components of endoscopy system 10, such as suction pump 26 (FIG. 1) and treatment generator 44 (FIG. 2).

FIG. 3C a schematic cross-sectional view taken along section plane 3C-3C of FIG. 30 showing an elevator 54. Elevator 54 can comprise deflector 55 that can be disposed in space 53 of housing 52. Deflector 55 can be connected to wire 57, which can extend through tube 59 to connect to handle section 32. Wire 57 can be actuated, such as by rotating a knob, pulling a lever, or pushing a button on handle section 32. Movement of wire 57 can cause rotation, e.g., clockwise, from a first position of deflector 55 about pin 61 to a second position of deflector 55, indicated by 55'. Deflector 55 can be actuated by wire 57 to move the distal portion of instrument 63 extending through window 65 in housing 52.

Figure 5:
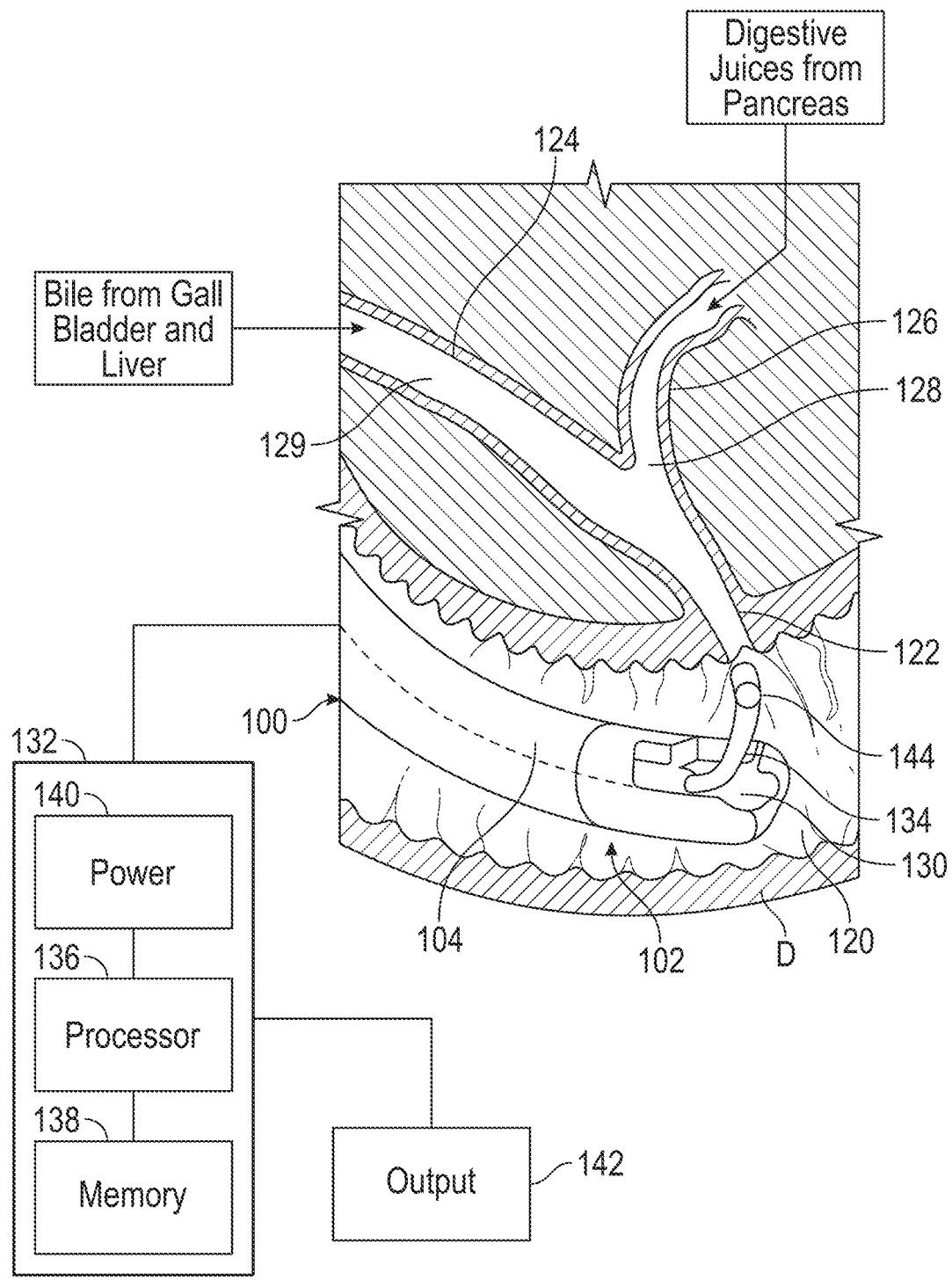
FIG. 5 is a schematic illustration of a distal portion of an endoscope including a biliary diagnostic device according to the present disclosure positioned in a duodenum.

Housing 52 can comprise accommodation space 53 that houses deflector 55. Instrument 63 can comprise forceps, a catheter, or the like that extends through lumen 62. A proximal end of deflector 55 can be attached to housing 62 at pin 61 provided to the rigid tip 21. A distal end of deflector 55 can be located below window 65 within housing 62 when deflector 55 is in the lowered, or un-actuated, state. The distal end of deflector 55 can at least partially extend out of window 65 when deflector 55 is raised, or actuated, by wire 57. Instrument 63 can slide on angled ramp surface 51 of deflector 55 to initially deflect the distal end of instrument 63 toward window 65. Angled ramp surface 51 can facilitate extension of the distal portion of instrument 63 extending from window 65 at a first angle relative to the axis of lumen 62. Angled ramp surface 51 can include groove 69, e.g. a v-notch, to receive and guide instrument 63. Deflector 55 can be actuated to bend instrument 63 at a second angle relative to the axis of lumen 62, which is closer to perpendicular that the first angle. When wire 57 is released, deflector 55 can be rotated, e.g., counter-clockwise, back to the lowered position, either by pushing or relaxing of wire 57. In examples, instrument 63 can comprise a cholangioscope or auxiliary scope 134 (FIG. 5).

Side-viewing endoscope camera module 50 of FIGS. 3A-3C can include optical components (e.g., objective lens 60, prism 66, imaging unit 67, wiring 68) for collection of image signals, lighting components (e.g., illumination lens 58, light transmitter 64) for transmission or generation of light. Endoscope camera module 50 can also include a photosensitive element, such as a charge-coupled device ("CCD" sensor) or a complementary metal-oxide semiconductor ("CMOS") sensor. In either example, imaging unit 67 can be coupled (e.g., via wired or wireless connections) to image processing unit 42 (FIG. 2) to transmit signals from the photosensitive element representing images (e.g., video signals) to image processing unit 42, in turn to be displayed on a display such as output unit 18. In various examples, imaging and control system 12 and image processing unit 67 can be configured to provide outputs at desired resolution (e.g., at least 480p, at least 720p, at least 1080p, at least 4K UHD, etc.) suitable for endoscopy procedures.

In order to facilitate customization, assembly, disassembly, cleaning and sterilization, endoscope 14 can be built with modular components, as is described with reference to FIG. 4.

Figure 4:
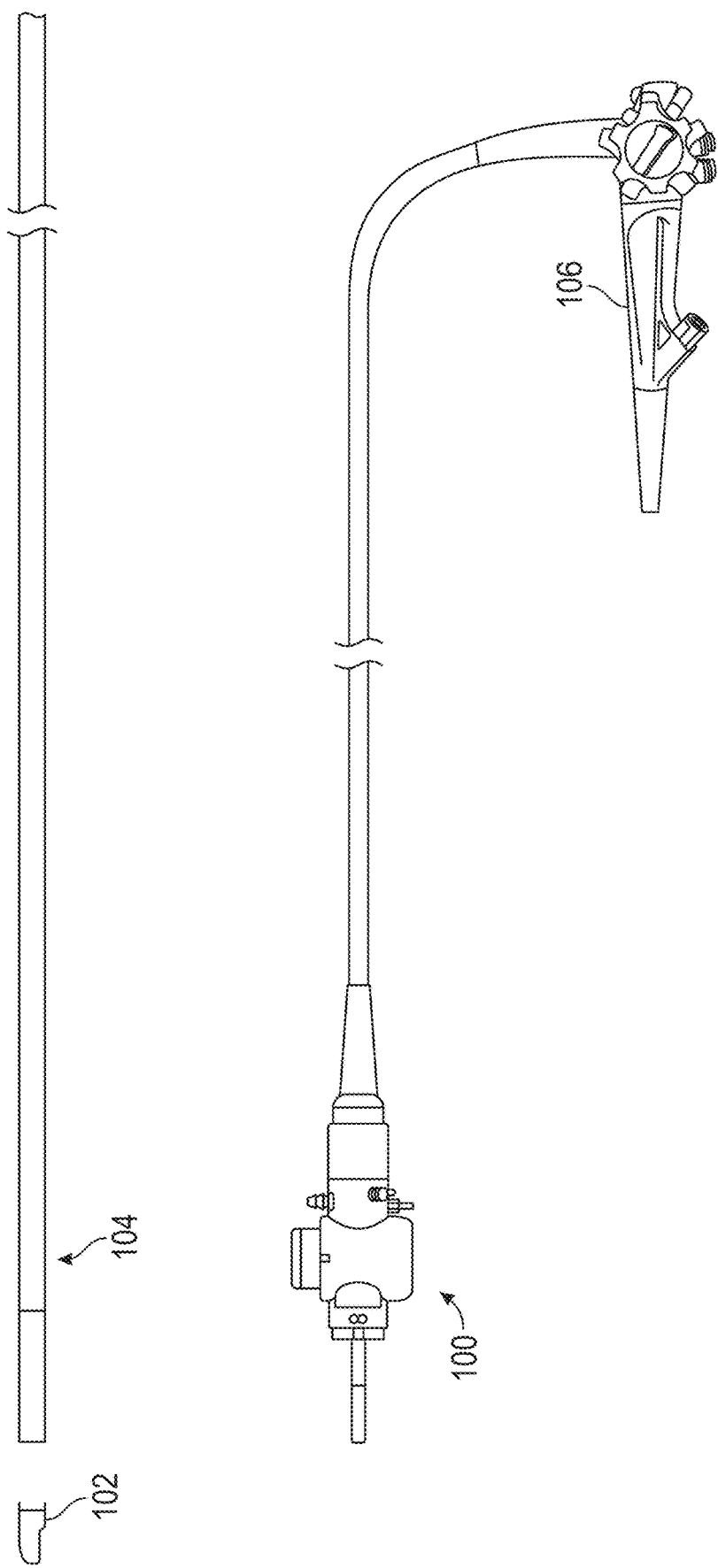
FIG. 4 is a schematic view of a modular endoscope suitable for use as the endoscope of FIGS. 1-3C comprising a camera module, an insertion section module, and a navigation and control module that are configured to be detachable from each other.

FIG. 4 is a schematic view of modular endoscope 100 suitable for use as endoscope 14 and with endoscope camera module 50 of FIGS. 3A-3C. Modular endoscope 100 can comprise a modular detachable functional module 102, insertion section module 104 and navigation and control module 106. Modules 102, 104 and 106 can comprise components including customizable features and components. As such, modular endoscope 100 can be custom-built to perform a specific procedure for a specific patient. Individual modular components can be configured as reusable or disposable components. Therefore, inexpensive or difficult to clean components can be disposed of and expensive or easy to clean components can be reused after appropriate cleaning and sterilizing.

Functional module 102 can comprise functional section 30, camera module 50 or other types of modules. Functional module 30 can include one or both of an imaging device, a therapeutic device, an ancillary therapeutic device, and a biliary diagnostic device, as well as other devices as is described herein.

In examples, functional module 102 can comprise camera modules of the endoscopes described in U.S. provisional patent application 63/024,674 filed on May 14, 2020, titled, "Endoscope with a Low-Profile Distal Section," the entire contents of which is hereby incorporated by reference.

Navigation and control module 106 can comprise handle section 32, cable section 34 and coupler section 36 of FIGS. 1 and 2.

In examples, navigation and control module 106 can comprise navigation and control modules of the endoscopes described in U.S. provisional patent application 62/951,157 filed on Dec. 20, 2019, titled, "Modular Endoscope with Detachable and Selectively Disposable Components," the entire contents of which is hereby incorporated by reference.

Insertion section module 104 can comprise a tubular element, sheath or shaft upon and within which functional module 102 can be mounted for insertion into anatomy of a patient.

In examples, insertion section module 104 can comprise insertion section 28, which can be configured to include one or more of the sheath and shaft components of U.S. provisional patent application 63/017,901 filed on Apr. 30, 2020, titled, "Insertion Sheath for Modular Endoscope with Detachable and Selectively Disposable Components," the entire contents of which is hereby incorporated by reference.

As mentioned previously, components of endoscope 14 can be modular, as shown by modular endoscope 100 of FIG. 4, such that they can be attached by an operator to initially configure the device for use with a patient, and can be detached by the operator after use with the patient. In other examples, the modular components can be assembled and disassembled by a manufacturer or a decommissioning service without action from the operator. In an example, FIG. 4 illustrates endoscope 14 of FIG. 2, wherein components thereof are shown in a detached state. While FIG. 4 illustrates endoscope 14 as being constructed from three modular components (functional module 102 [functional section 30]), navigation and control module 106 [handle section 32], insertion section module 104 [insertion section 28]), additional or fewer components are contemplated, depending on the surgical procedure to be performed with the configuration of endoscope 14 constructed or designed by the operator. Each of functional module 102, navigation and control module 106, and insertion section module 104 can be detachable from each other. Furthermore, each of modules 102, 104 and 106 can be disposed after a single clinical use. Alternatively, each of modules 102, 104 and 106 can be constructed using materials that would permit several clinical uses. In such cases, modules 102, 104 and 106 can be constructed to withstand sterilization after each clinical use.

In certain advantageous aspects, the modular construction of endoscope 14 of FIG. 2 and modular endoscope 100 of FIG. 4, and as discussed herein, can permit mixing and matching of disposable and reusable modules such that some modules can be reused, such as expensive and/or easy to clean modules, and some modules can be disposable, such as simple and/or difficult to clean modules. For example, certain modules can be detached from the endoscope after a clinical use for sterilization, reprocessing, and reuse for subsequent clinical uses, while the remaining modules can be disposed. For instance, there have been concerns with inadequate reprocessing of portions of duodenoscopes (e.g., elevator portions). As a result, single-use endoscopes that can be disposed after a single clinical use (to prevent infection between uses) have been developed. However, currently available single-use endoscopes, wherein the entire endoscope is disposed of, can be constructed using lower cost materials resulting in a lower price for the endoscope in order to remain competitive per clinical use. In many clinical instances, lower cost materials can lead to poorer clinical performance (e.g., lower quality images, inadequate maneuverability, insertion section module damage during insertion, poorer ergonomic of endoscope handle, etc.). As such, inferior components can result in practitioners preferring not to use such devices.

Accordingly, modular endoscopes 14 and 100 of FIGS. 2 and 4, and others described or incorporated herein are advantageously constructed such that the end user (e.g., health care providers and facilities) can recover certain modules of endoscope 14 for reuse, while disposing infection prone areas after a single clinical use. In addition, portions of the endoscope that are intended for reuse can be constructed to reduce accumulation of biological materials (such as be being fully encapsulated), and can additionally be fluidly isolated from infection prone areas. Such configurations promote the use of a combination of higher quality (higher cost) reusable components usable over multiple clinical uses, and lower cost, disposable portions, while reducing infection risk, and achieving desired clinical performance. Not only can the disposable components be constructed to include features only needed for the specifically-built procedure, but the materials and construction can be built to only survive one-time use, both of which help reduce the cost of the disposable components. For example, insertion sheaths can be built to survive the stress of only a single operation and does not need to be robustly constructed to survive repetitive stresses of multiple procedures.

In examples, endoscope 100 of FIG. 4 can comprise a duodenoscope, functional module 102 can be configured as a reusable camera module, navigation and the control module 106 can comprise a reusable handle module, and insertion section module 104 can comprise a disposable unit having multiple lumens. Accordingly, the camera module and the navigation and control module can each include connectors that can maintain each of the camera module and the navigation and control module in an attached state to the insertion section module during use with a patient. After each use, the camera module and the navigation and control module can be separated (e.g., using connectors or attachment mechanisms, and reprocessed for subsequent use with a new insertion section module. Conversely, the used insertion section module can be disposed after a single use.

Additionally, the connectors of the camera module and the navigation and the control module as well as the camera module and the navigation and the control module can be constructed of materials and engineered to reduce any ingress of biological materials and can optionally be constructed in a fluid-tight manner.

Modular endoscope 100 can be configured for either a "side-viewing" configuration (as shown in FIGS. 3A-3C) or an "end-viewing" configuration. In examples, wherein modular endoscope 100 is configured as a side-viewing device (e.g., side-viewing duodenoscope), the distal modular section (e.g., camera module) can be offset from a longitudinal axis of the middle modular section (e.g., insertion module), to accommodate additional components (e.g., elevator mechanisms and the like). In other examples, wherein modular endoscope 100 is configured as an end-viewing device (e.g., gastroscope, colonoscope, cholangioscope, etc.), the distal modular section (e.g., camera module) can be generally co-axially positioned along a longitudinal axis of the middle modular section (e.g., insertion module).

FIG. 5 is a schematic illustration of distal portion of an endoscope 100 according to the present disclosure positioned in duodenum D. Duodenum D can comprise duct wall 120, sphincter of Oddi 122, common bile duct 124 and main pancreatic duct 126. Duodenum D comprises an upper part of the small intestine. Common bile duct 124 carries bile from the gallbladder and liver (not illustrated) and empties the bile into the duodenum D through sphincter of Oddi 122. Main pancreatic duct 126 carries pancreatic juice from the exocrine pancreas (not illustrated) to common bile duct 124.

Endoscope 100 can comprise insertion section module 104 and function module 102. Function module 102 can comprise elevator portion 130. Endoscope 100 can further comprise biliary diagnostic device 132 and auxiliary scope 134. Biliary diagnostic device 132 can comprise processor 136, memory 138 and power source 140. As discussed below, biliary diagnostic device 132 can be integrated into endoscope 100, such as on functional module 102, insertion section module 104 or auxiliary scope 134, such as via electrode 144.

In certain duodenoscopy procedures (e.g., Endoscopic Retrograde Cholangio-Pancreatography, hereinafter "ERCP" procedures) an auxiliary scope (also referred to as daughter scope, or cholangioscope), such as auziliary scope 134, can be attached and advanced through the working channel, (e.g., within insertion section module 104) of the "main scope" (also referred to as mother scope or duodenoscope), such as endoscope 100. As discussed in greater detail below, auxiliary scope 134 can be guided into sphincter of Oddi 122. Therefrom, a surgeon operating auxiliary scope 134 can navigate auxiliary scope 134 toward the gall bladder or liver to perform various procedures. As such, the surgeon can navigate auxiliary scope 134 past entry 128 of main pancreatic duct 126 and into passage 129 of common bile duct 124. Biliary diagnostic device 132 can facilitate navigation to the gall bladder or liver, and bypassing of main pancreatic duct 126, by sensing for biological matter originating from the gall bladder or liver in common bile duct 124. The smaller auxiliary endoscope can have its own functional devices, such as a light source, accessories, and biopsy channel, for therapeutic procedures.

According to several examples, endoscope 100 can be suitable for cholelithotomy (for instance, the removal of gallstones which can build up as a calculus within the gallbladder or other portions of the pancreobiliary duct). Located on the right side of the abdomen under the liver, the gallbladder can store and releases bile, through the common bile duct, for instance, during digestion. During the storage of the bile, the gall bladder can also concentrate (e.g., draw water out of) the liver bile and crystals from the bile solution may develop, which can agglomerate, and/or take many shapes, including forming a sandy like particle. The creation of these crystals depends upon the solubility of the three components present in bile, such as, cholesterol, bile acids and phospholipids. As the balance of constituents such as cholesterol, bile acids and phospholipids begins to vary, one or more elements of bile can move out of solution and may create crystals.

In several examples, crystals can aggregate and grow into particles and can continue to develop within the gallbladder (e.g., if not excreted) and may develop through the stages of 'gravel' and 'stones.' According to several aspects, sizes of crystals can be less than the size of a particle. Furthermore, in some aspects, the size of crystals and/or particles can be less than the size of gravel. Additionally, in some instances, the size of crystals can be less than the size of stones. In an example, the size of the crystal can be less than the size of the particle, gravel and stone. In another example, the size of the particle can be less than the size of gravel and stone, and in a further example, the size of the gravel can be less than the size of a stone. In still further examples, the sizes of crystals, particles, gravel and stone can follow the relationship ($D_{crystal} < D_{particle} < D_{gravel} < D_{stone}$), where in "D"

represents size (a characteristic dimension, such as length, surface area, one or more cross-sectional areas and the like).

In some aspects, the larger gravel or stone size growths move within the gallbladder. If they are too large to pass through the single gallbladder bile duct, the growths pass in front of the gallbladder bile duct and create an intermittent obstruction. This obstruction can prevent the gallbladder from being able to empty and this results in inflammation and irritation of the gallbladder. In some cases it can also lead to infection of the gallbladder, where the gallbladder may fill with pus.

According to a few cases, if the stone or gravel moves away from the bile duct and the pressure is relieved, the gallbladder may still be affected by the experience with localized scaring potent occurring, increasing the severity at the next passage of the stone over the duct. Some such occurrences can lead to cholelithiasis, (also referred to as 'Gallbladder disease'). Sometimes the stone can become captured in the bile duct itself. Depending on the location of this blockage, the stone can cause blockage of all liver bile secretions or worse, if the stone sticks at the ampulla of vater, the pancreatic fluids can also become blocked. This can result in pancreatitis as well as cholelithiasis as the common bile duct is shared between the pancreas and liver/gallbladder as a way of communicating their associated fluids to the digestive tract.

One surgical procedure to address stone formation and/or remove the calcifications at the same time is called cholecystectomy, which can be performed invasively through the skin and can often be performed laparoscopically (unless there are associated complications such as irritation and a large number of stones within the bile duct, then an open procedure might be undertaken). An alternative to Cholocystectomy can use natural orifice entry for the procedure but may leave the gallbladder in place. This procedure can, in some instances be referred to Endoscopic Retrograde CholangioPancreatoscopy (ERCP). ERCP can use a viewing system (e.g., a duodenoscope, illustrated in FIG. 3A-3C) combined with a functional ability (inherent to the camera or in conjunction with) introduced into the patient via the mouth, esophagus, stomach and/or duodenum to allow access to the biliary system, for instance, without the need for surgical access incisions.

With continued reference to FIG. 5, during biliary procedures (e.g., ERCP), the cystic duct and common bile duct may be enlarged through surgical means varying from dilation through cannulation to energy devices (such as a sphincterotome) cutting tissue within the duct to enlarge the internal duct diameter. This allows for the extraction and expulsion of gallstones during the procedure as well as reducing the risk of future stone entrapment.

With continued reference to FIG. 5, the common bile duct is a shared duct between the liver, gallbladder and pancreas. The common bile duct may have a number of bifurcations, which may pose challenges for a practitioner trying to identify the correct duct pathway to the gallbladder, for instance, during biliary procedures (e.g., ERCP).

A clinician may have to either rely on previous knowledge of patient anatomy (and the expected angular difference between the two ducts) or use available technology or a combination to make a positive identification of the common bile duct. The surgeon can use fluoroscopy to identify the bile duct from the pancreatic duct. However, if not required for other elements of the procedure, fluoroscopy can be a procedure-invasive technology, and can involve particular set-up situations and associated personal protective equipment.

Several implementations of the present disclosure aim to not only provide an alternative method for facilitating identification of the correct duct (for instance, prior to dilation), but also to predict what type of stone formation has occurred. Understanding the type of stone formation via the liver secretions can also provide the surgeon insight as to whether a change in eating habits or pharmaceuticals may also reduce the risk of future recurrence of the issue.

According to aspects of the present disclosure, referencing FIGS. 6A-10, biliary diagnostic device 132 is provided that utilizes the difference in properties between bile and pancreatic fluid. Biliary diagnostic device 132 according to several aspects can facilitate navigating, cannulating or cutting areas in the vicinity of the common bile duct, for example, prior to, during or after biliary (e.g., ERCP) procedures. The bile created by the liver stored in the gallbladder and communicated through the bile ducts can have unique properties than can be used to positively identify the bile duct from the pancreatic duct(s).

The biliary diagnostic devices of the present disclosure, such as biliary diagnostic device 132 and biliary diagnostic device 222 (FIG. 12B), according to several aspects, can rely on electrical properties of bile. For instance, bile can have electrical conductivity higher than several fluids or portions of the human body. The biliary diagnostic device can, in one or more implementations, include components capable of sensing electrical conductivity, such as electrode 144, and positively identify the bile duct from the pancreatic duct. In other examples, the biliary diagnostic device can determine phase angle of a fluid.

Figure 12A:
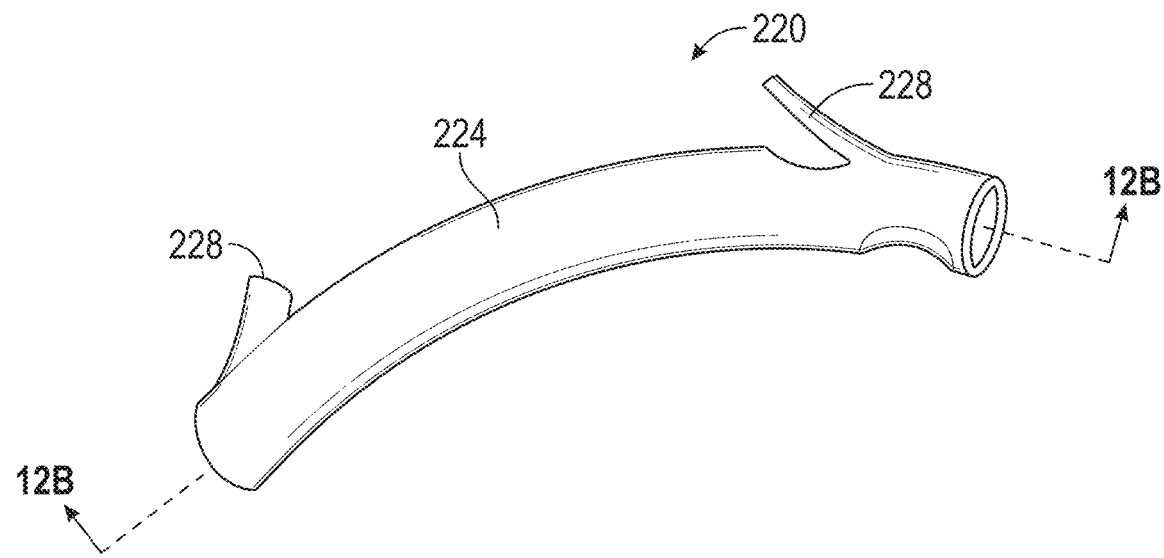
FIG. 12A is a perspective view of a stent incorporating a biliary diagnostic device of the present disclosure.
Figure 12B:
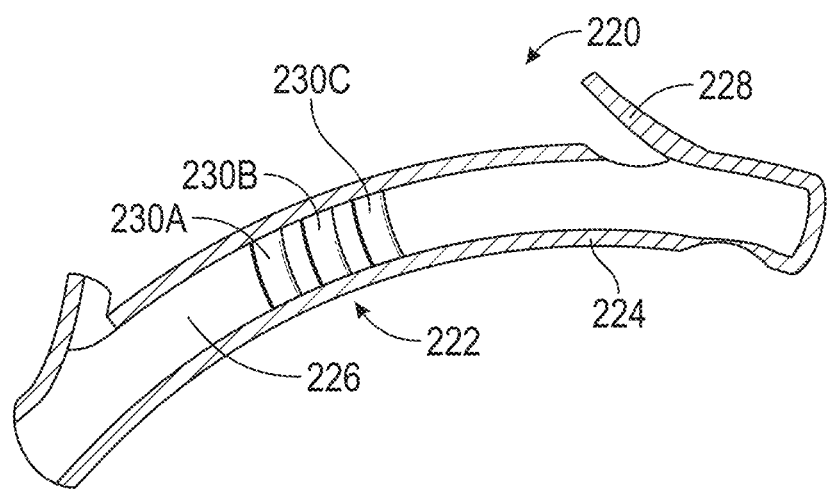
FIG. 12B is a cross-sectional view of the stent of FIG. 12A taken at the plane 12B-12B showing electrodes of the biliary diagnostic device.

FIGS. 6A-10 illustrate various examples of biliary diagnostic device 132 of the present disclosure, which can be provided as a part of endoscope 14 or endoscope 100. In examples, biliary diagnostic device 132 can be provided on a distal portion of endoscope 100. In several examples, biliary diagnostic device 132 can be provided on a duodenoscope and/or a cholangioscope. In still further aspects, biliary diagnostic device 132 can operate in communication with and/or be attachable to one or more endotherapy accessories (e.g., guidewire, sphincterotome, dilation balloons, guide catheter, access sheaths, biliary stents etc.) usable during a biliary procedure (e.g., ERCP procedure or other types of biliary procedures). As illustrated in FIGS. 12A and 12B, in examples, biliary diagnostic device 222 can be provided on stent 220.

Figure 6A:
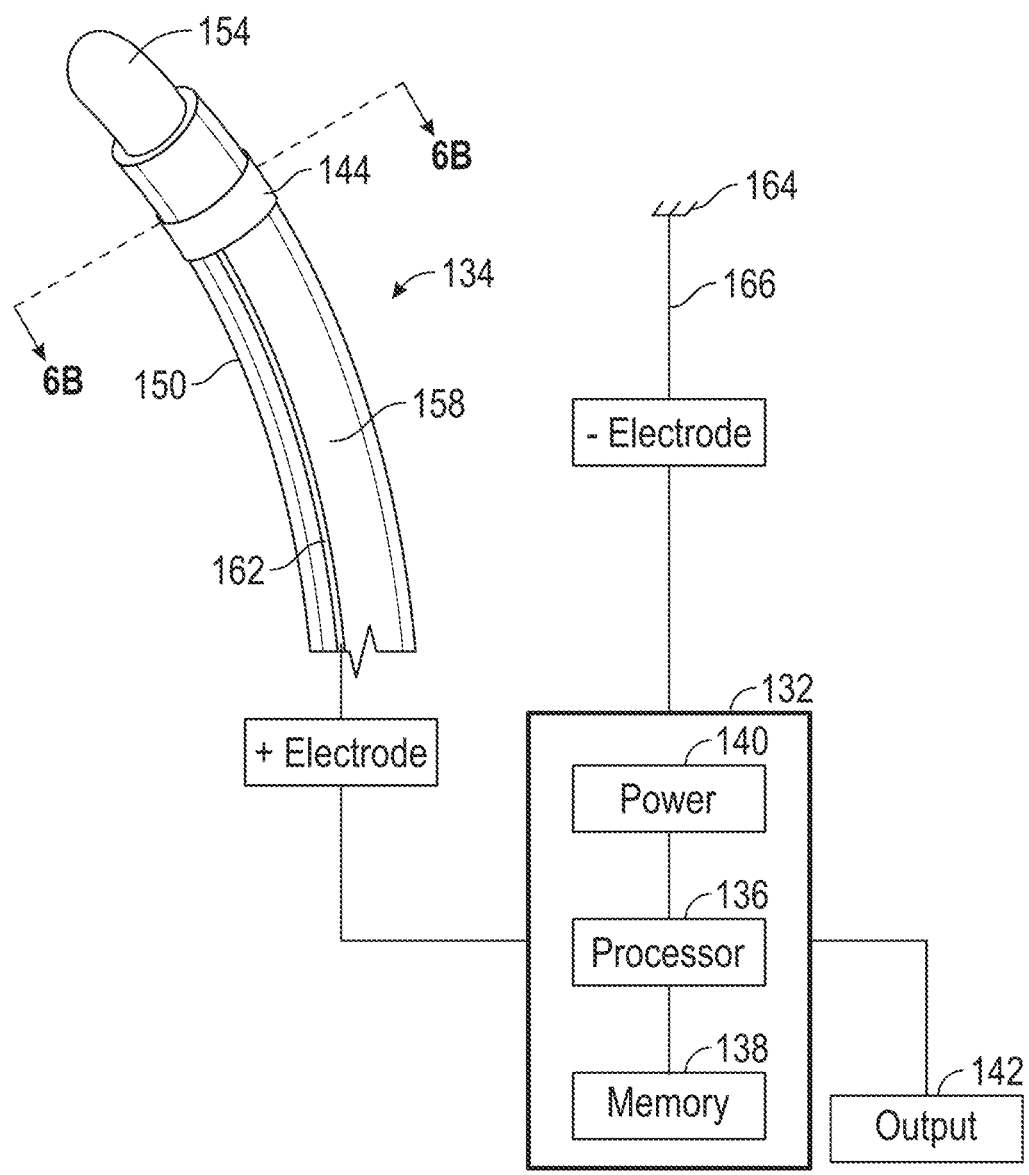
FIG. 6A is a perspective view of a first example of a biliary diagnostic device of the present disclosure comprising a single electrode ring configured to function as a positive electrode.
Figure 6B:
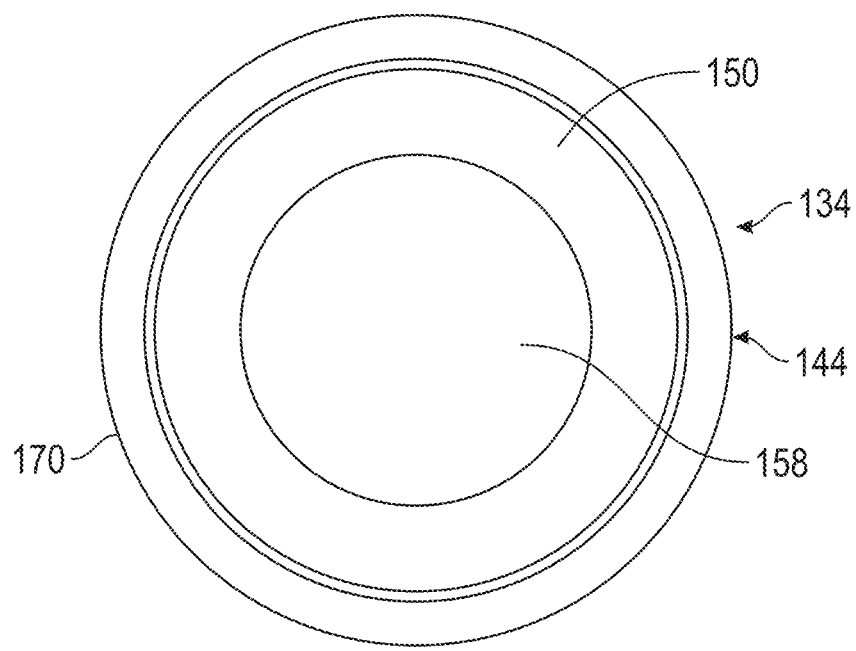
FIG. 6B is a schematic cross-sectional view taken along the plane 6B-6B of FIG. 6A showing a first example of an electrode shape.
Figure 6C:
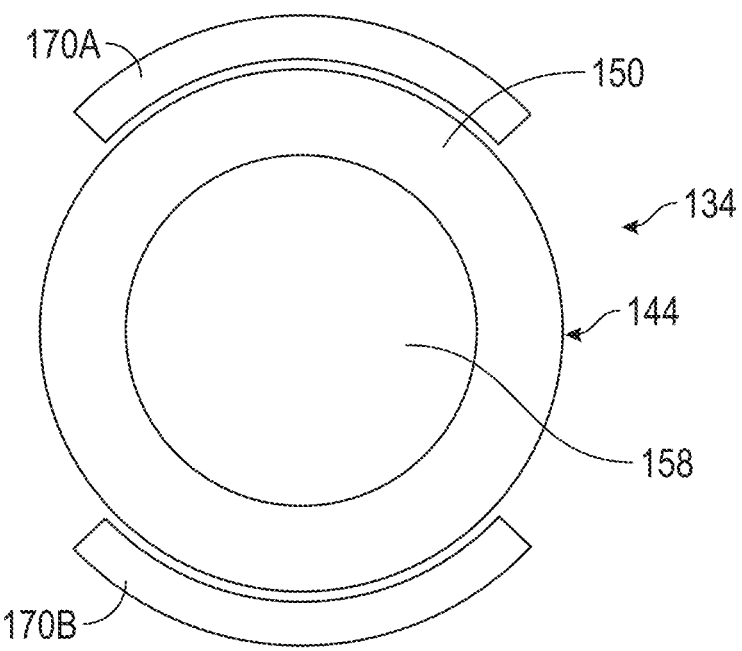
FIG. 6C is a schematic cross-sectional view taken along the plane 6B-6B of FIG. 6A showing a second example of an electrode shape.
Figure 7:
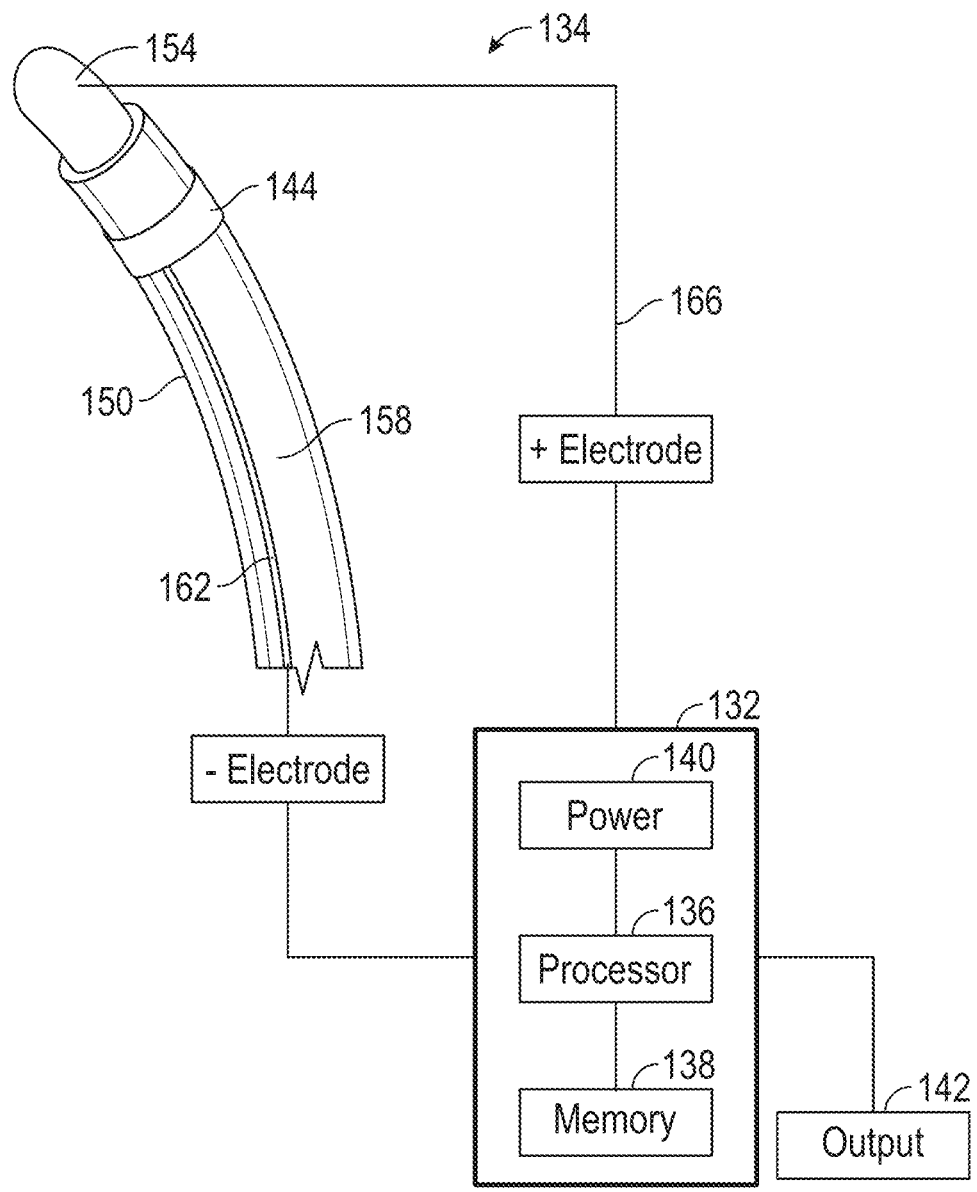
FIG. 7 is a perspective view of a second example of a biliary diagnostic device of the present disclosure comprising a single electrode ring configured to function as a negative electrode and a guidewire configured to function as a positive electrode.
Figure 8:
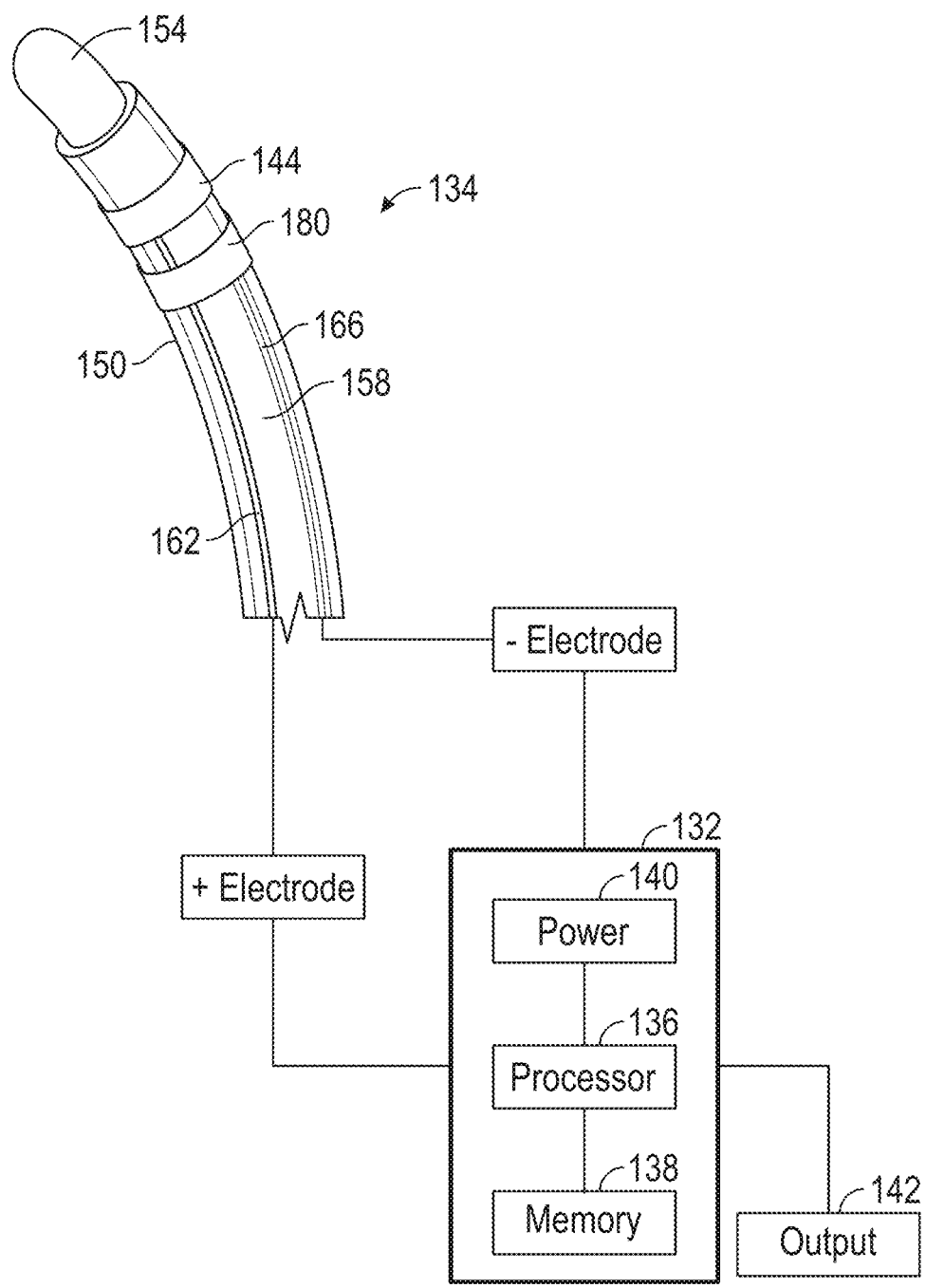
FIG. 8 is a perspective view of a third example of a biliary diagnostic device of the present disclosure comprising a pair of electrode rings configured to function as positive and negative electrodes.
Figure 9:
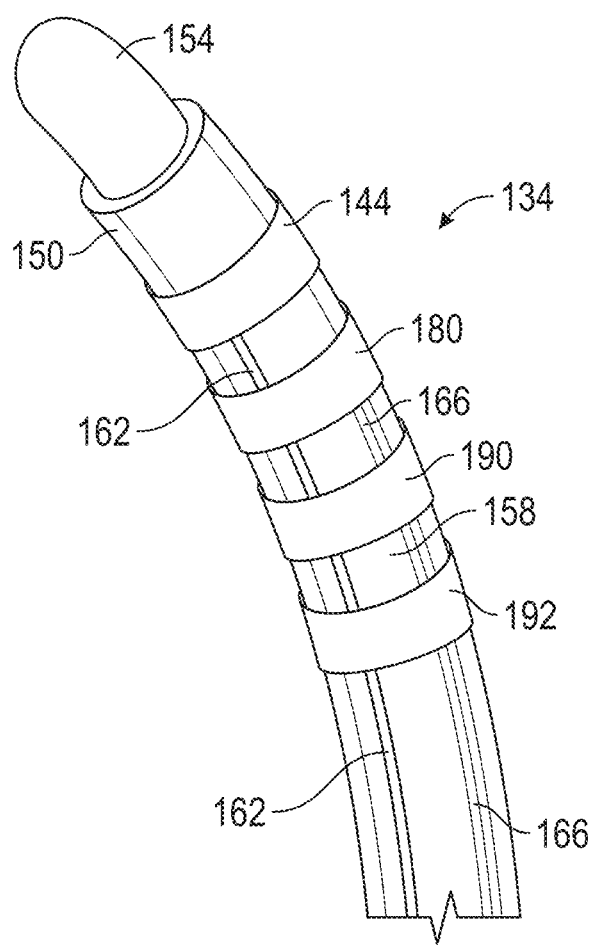
FIG. 9 is a perspective view of a fourth example of a biliary diagnostic device of the present disclosure comprising a plurality of electrode rings configurable as discrete or combined biliary diagnostic sensors.

According to an aspect, biliary diagnostic device 132 can include one or more sensors, as is illustrated in FIGS. 6A-10. In examples, the sensors can include electrical components (e.g., electrodes) on portions of the anatomy into which auxiliary scope 134 is inserted. Each of the sensors can include a positive electrode and a negative electrode. As shown in FIG. 6A, electrode 144 can be configured as a positive electrode and tissue can be configured as a negative electrode. As shown in FIG. 7, electrode 144 can be configured as a negative electrode and guidewire 154 can be configured as a positive electrode. In other examples, as shown in FIGS. 8 and 9, a plurality of electrodes can be provided to function as one or more sensors. Positive and negative electrode can comprise electrically conducting rings or pads that can be connected to an energy sources, such as power source 140, that can direct current between the electrodes. The sensors can, for instance, be electrically isolated from each other. For example, the positive and negative electrodes can be isolated using dielectric material positioned along shaft 150. The sensors can be disposed on a surface (e.g., outer surface, interior surface, working channel, etc.) of an endoscope, such as auxiliary scope 134.

In alternative examples, the sensors can be disposed at a leading face or on, or around the leading face of an endotherapy instrument.

According to several implementations, an electrical signal, such as from power source 140, can be passed between the two electrodes, e.g., electrode 144 and the anatomy. Further, electrical properties and/or variations thereof (e.g., impedance, resistance or phase angle of the tissues) at one or more locations (e.g., between the device's tip) can be detected by the sensors to identify the presence of bile, and further guide, cannulate endotherapy instruments or facilitate identification of the bile duct from the pancreatic duct. Several implementations of the biliary diagnostic device can reduce the instances in which fluoroscopy might be involved to identify the appropriate duct.

Bile fluid can have properties different from pancreatic fluid or other anatomical features (e.g., tissue, etc.). For instance, the sensors can detect one or more electrical properties of bile and surrounding anatomy (e.g., tissue, pancreatic duct, pancreatic fluid, etc.), and delineate the bile duct from surrounding areas (e.g., tissue, pancreatic duct, pancreatic fluid, etc.) if one or more electrical properties (e.g., resistance, impedance, phase angle, and the like) at the tip of the device are utilized, then it is known that the electrical properties (e.g., electrical conductivity) of bile can be detected. For instance, electrical conductivity of bile can be greater than that of the surrounding tissue or pancreatic juice.

In an example, biliary diagnostic device 132 can be calibrated to use electrical properties (e.g., resistance, impedance, phase angle, and the like) as an indicator of bile presence. In some instances, the tissue in the vicinity of bile can be more electrically conductive than any other tissues in the pancreobiliary area.

In examples, biliary diagnostic device 132 can use electrical conductivity, for example, optionally, either in a low power DC or low power RF output, such as from power supply 142. In further optional implementations, biliary diagnostic device 132 can be operative communication with one or more output devices, such as output device 142, which can comprise, for example, endoscopy or endotherapy systems with integrated displays, or physician consoles, touch-input devices, imaging and control system 12 and the like. In particular, output device 142 can comprise output unit 18 of imaging and control system 12. Output device 142 can actively, e.g., continuously, at several instances during a pancreobiliary procedure, and the like, report back to the user whether the tissue being encountered is of increasing or decreasing conductivity, as is shown in FIGS. 13-15.

Figure 11:
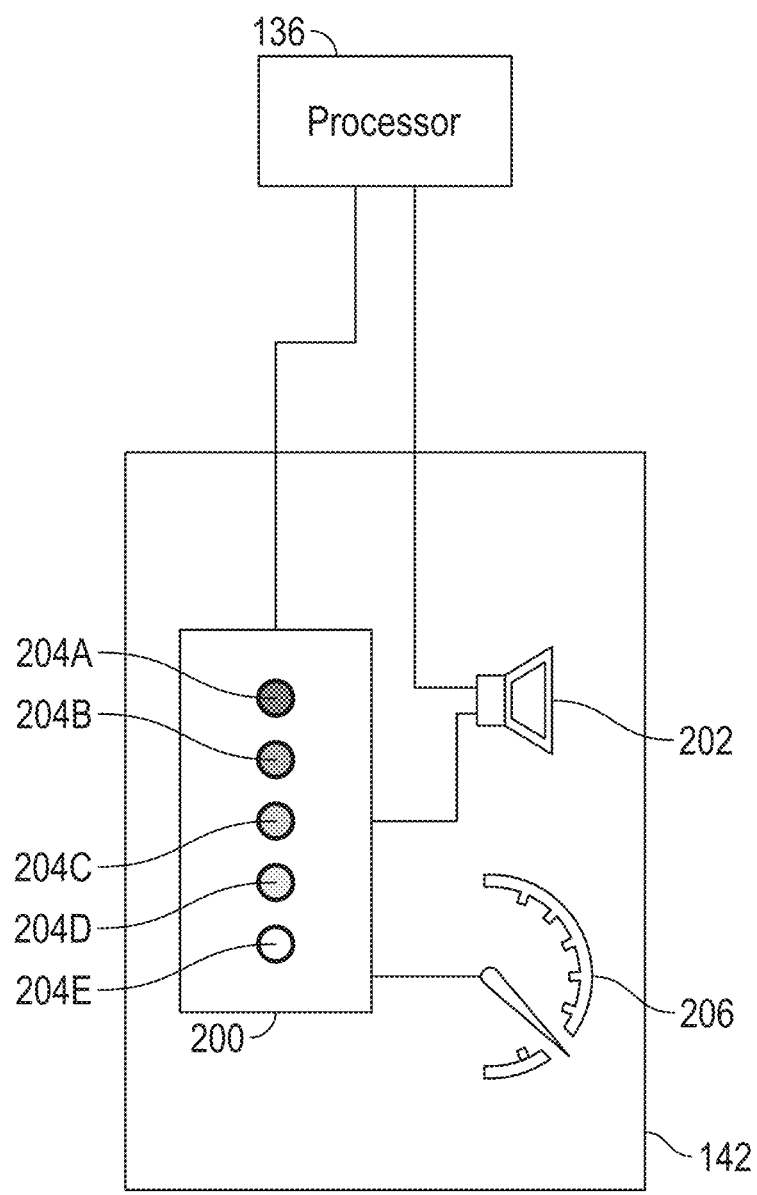
FIG. 11 is a schematic view of an output device suitable for use with the biliary diagnostic devices disclosed herein.
Figure 13:
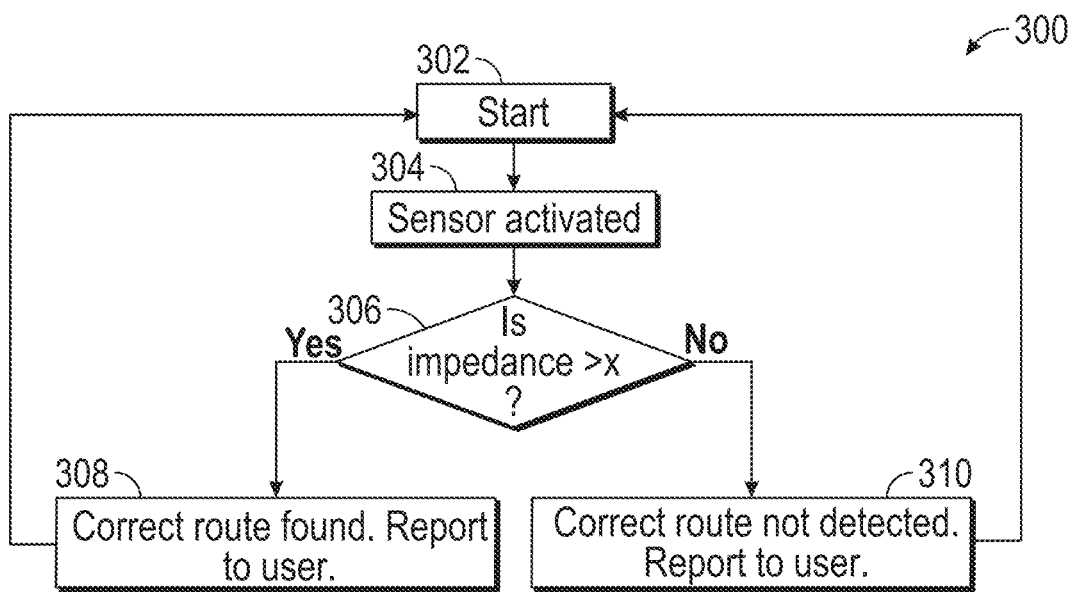
FIG. 13 is block diagram illustrating a first method for performing a chemical analysis using the biliary diagnostic devices of the present disclosure comprising a single-stage impedance analysis for route sensing.
Figure 14:
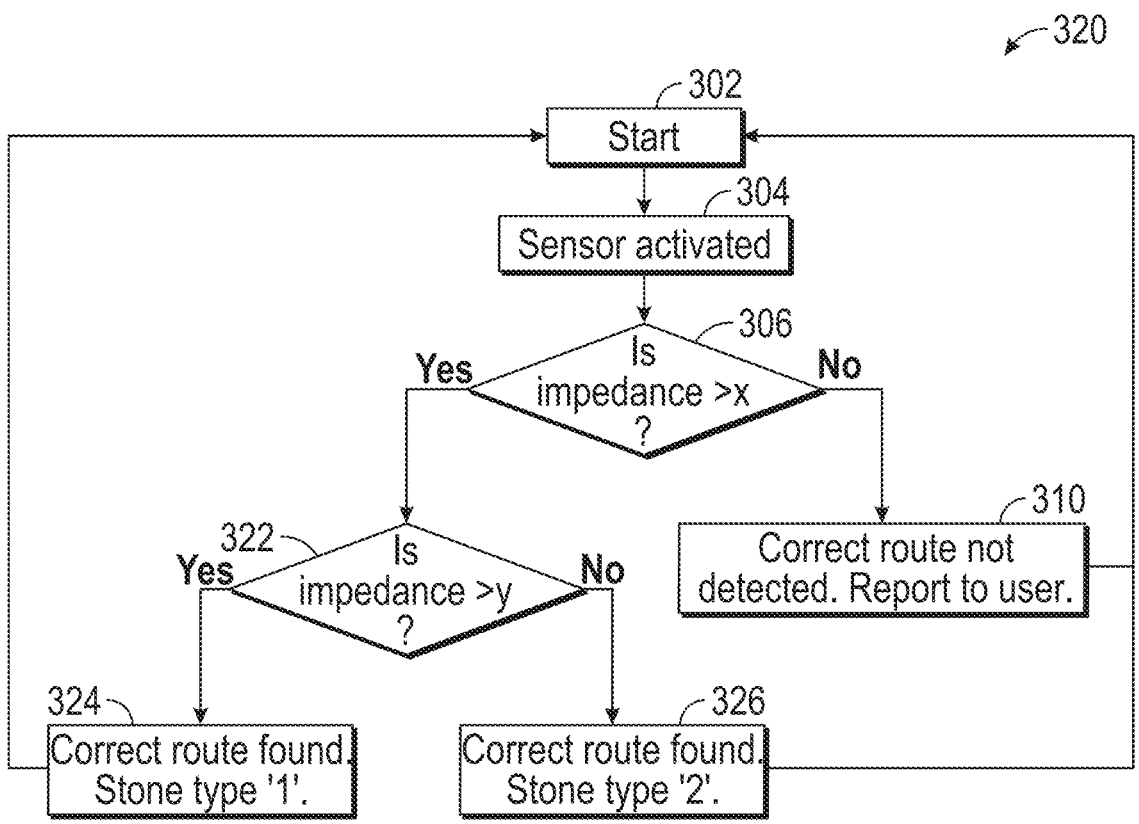
FIG. 14 is block diagram illustrating a second method for performing a chemical analysis using the biliary diagnostic devices of the present disclosure comprising a double-stage impedance analysis for route and stone sensing.
Figure 15:
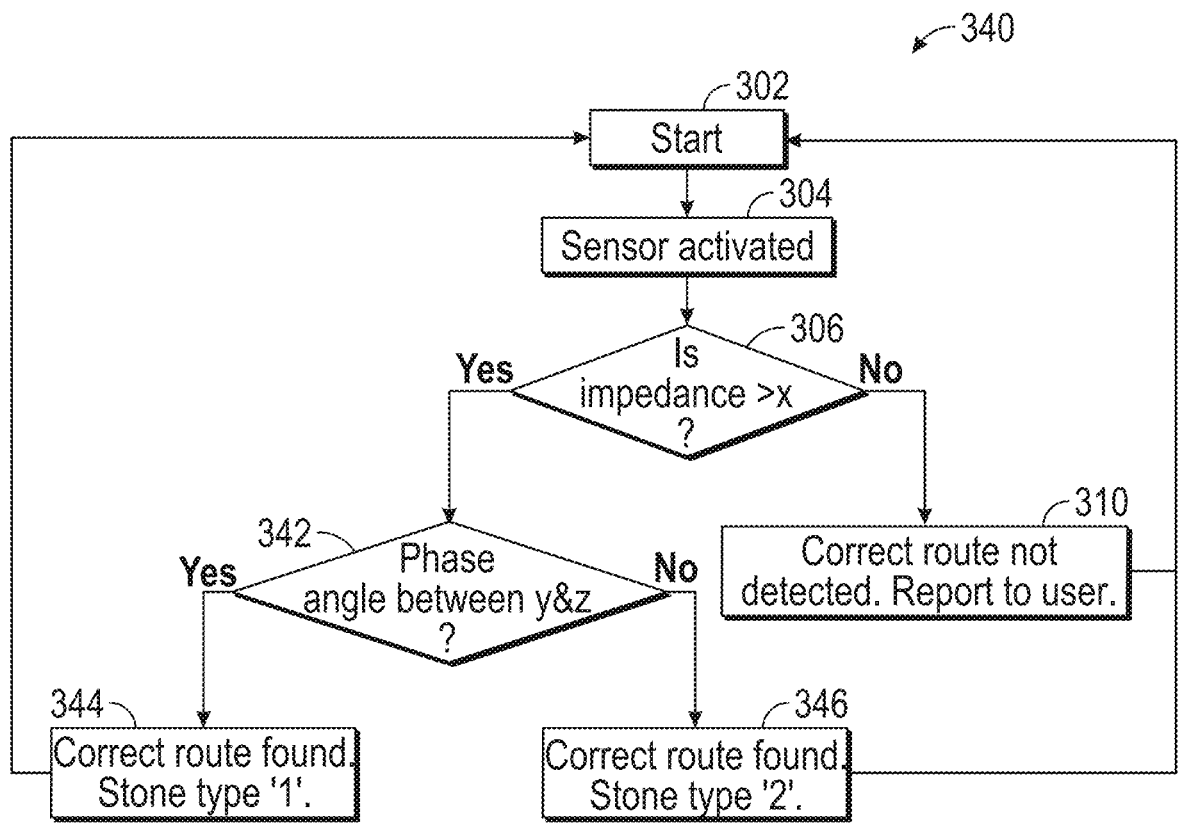
FIG. 15 is block diagram illustrating a third method for performing a chemical analysis using the biliary diagnostic devices of the present disclosure comprising a double-stage impedance and phase angel analysis for route and stone sensing.

One or more optional implementations can provide different reports to the user, as seen in flow diagrams of FIGS. 13-15 and output device 142 of FIG. 11. Another optional example can report to the user whether the conductivity has met a predetermined level, indicative of liver bile and informs the user of such. It can also inform the user if a more-concentrated version is identified (more conductive) if the conductivity reaches a value where the conductivity is indicative of concentrated fluid retained in the gall bladder. Another optional implementation can inform the user if a concentrated bile material is detected. Another optional implementation can inform the user if no bile fluid is detected (concentrated or otherwise). Another implementation can provide a combination or selection of the above information feedback elements.

Further optional implementations can provide other features using distinctive properties of bile. For instance, instead of sensing electrical conductivity, the device can sense impedance or phase difference between bile and surrounding anatomical features (e.g., surrounding tissue, pancreatic fluid, etc.) can be detected.

Referring again to FIGS. 6A-10, in several aspects, the location and number of electrodes and sensors formed therefrom can be varied. For instance, in FIGS. 6A and 10, one electrode can be located in vivo at the distal section of the endoscope or an endotherapy instrument, and the second electrode can be located elsewhere (e.g., extracorporeally) or electrically coupled to a natural or floating ground. In other aspects, as seen in FIGS. 7-10, and 12B, a plurality of electrodes can be placed on or close to the front (distal) edge of the endoscope or the endotherapy instrument. In either scenario, interrogative signals associated with one or more sensors formed by the electrodes can be suitable for identifying the specific fluid signature.

As previously mentioned, different types of crystals are created when different chemical imbalances occur in the liver bile. The chemical difference can result in different electrical signatures. By sampling the electrical signature of the concentrated gallbladder fluid, the chemical imbalance can be identified and, optionally, the user can be informed, for instance, via one or more reports. This can subsequently lead to a greater understanding as to the cause of the crystal formation. Furthermore, this can be coupled with medicinal or lifestyle change options for the patient to reduce future incidences of a variety of biliary conditions. In some implementations, identification such as those disclosed here could be reported (e.g., directly or indirectly) to the user by comparing the measured diagnostics (e.g., sensed electrical properties) to one more preset values within the system. In optional embodiments, the diagnostic values can be provided directly to the surgeon, specialist, or to a diagnostic algorithm for further analysis and reporting.

As with many surgical and diagnostic instruments, the device according to several implementations can be disposable after being used in a single procedure and/or with a single patient, can be reused (e.g., with the same patient or with different patients) after a single procedure and/or can be reposable. Aspects and features of the device disclosed herein can be provided as a self-contained in a device (e.g., inserted into the working channel of an endoscope, and/or provided as a diagnostic device) and/or can be provided as a part (e.g., attachable, separable and/or integrated into the distal portion) of an endoscope and/or endotherapy instruments.

In instances where the device can be provided as a part of a suite of similar devices, each device can have a unique identifier system for each device type, so that the sensor can calibrate the readings specifically according to the device. For example, an identification circuitry (e.g., a chip) can be provided on the device to identify the type of device, and optionally, automatically set device-specific parameters (e.g., sensor calibration, settings for connectivity to other devices, device performance data, etc.). Several implementations can make the procedure more 'plug and play' and can reduce the need for clinical staff intervention in setting up the device.

While FIGS. 5-10 illustrate the biliary diagnostic devices as being provided on an elongate tubular element (e.g., an endoscope or an access sheath), similar configurations can also be provided as a part of a variety of endoteherapy instruments, such as guidewire, sphinctertome, monopolar, bipolar or cold cutting instruments (or a combination of disclosed instruments), or a stent as shown in FIGS. 12A and 12B.

In several optional implementations, the reports to the user can include a visual output, (e.g., a light illuminating diode or other visual, graphical displays, including on a console of an endoscopy or a surgery system), as shown in FIG. 11. Alternatively, other types of reports such as auditory, or detailed display of sensor readouts and/or diagnostic states (determined from previous diagnoses) can be displayed.

Systems described herein could also include more than one sensed quantity for improving accuracy of diagnostics and detection, for instance, phase angle and resistance or resistance and reactance, or impedance and phase angle etc. or greater sensor feedback multiples can provide even more accurate prediction of route direction and stone type. Multisensory feedback systems such as those disclosed herein can be envisaged for indicating the correct duct identification, indicating the stone type or a combination of duct identification and stone type. The sensor check system could be included within the device and be part of a standalone unit or integrated into other parts of the capital equipment used for such procedures, such as a surgical system or endoscopy system. The sensor system can also be part of a discrete reposable/disposable system or even capital system.

Implementations disclosed herein can result in many advantages, including improving identification of the common bile duct and/or biliary stones and facilitate preventing biliary stone formation (e.g., diets, pharmaceutical, lifestyle changes, etc.).

FIG. 6A is a perspective view of biliary diagnostic device 132 incorporated into auxiliary scope 134. Auxiliary scope 134 can comprise elongate shaft 150, guidewire 154 and biliary diagnostic device 132. Elongate shaft 150 can comprise lumen 158 into which guidewire 154 can be inserted. Biliary diagnostic device 132 can comprise electrode 144, lead 162, ground 164 and lead 166. Biliary diagnostic device 132 can be connected to processor 136, memory 138, power source 140 and output device 142, as previously described. In the example of FIG. 6A, electrode 144 can be configured to function as a positive electrode. Ground 164 can be configured to function as a negative electrode. Ground 164 can simply comprise tissue of the patient such that sensing occurs between the tissue and electrode 144.

Lead 162 and lead 166 can comprise conductors that can extend from electrode 144 and ground 164 through elongate shaft 150 to control module 106. Leads 162 and 166 can comprise elongate metal wires that can be joined to electrode 144 or any other electrode via suitable methods, such as welding or soldering, at distal ends. Proximal ends of leads 162 and 166 can be connected to processor 136.

Elongate shaft 150 can comprise an elongate body that is sufficiently rigid to support lead 162, lead 166 and electrode 144, but that is also sufficiently flexible to provide guided insertion through anatomy. In examples, elongate shaft 150 can comprise a medical grade polymer. Elongate shaft 150 can comprise one or more structures and layers, such as reinforcing structures and coating layers. In examples, elongate shaft 150 can include reinforcing wires embedded therein. In still other examples, elongate conductors can be provided by spiral windings provided inside elongate shaft 150, such as those used in endotracheal tubes including embedded spiral windings for reinforcement.

Additionally, elongate shaft 150 can comprise coatings to prevent or inhibit the adhesion of biological material to auxiliary scope 134. Such coatings can facilitate easier insertion of auxiliary scope 134 through the anatomy, such as by reducing friction. Additionally, coatings applied over exposed conducting components can prevent biological material from sticking to the electrical components and interfering with electrical signals generated or interpreted by sensing components, such as electrode 144. In an example, auxiliary scope 134 can be coated with polydimethylsiloxane. In examples, auxiliary scope 134 can be coated with other coating including nano-particles. Such coatings can be applied in thicknesses or made of compositions that do not, or do not substantially, inhibit sensing.

Metal wire conductors can be sheathed in an insulating coating that can be removed where contacting electrodes or performing sensing. Metal wire conductors can be embedded within the walls of elongate shaft 150 and elongate shaft 150 can provide insulation, with selective portions of elongate shaft 150 removed to allow sensing by the metal wire conductors or coupling to electrode 144. In additional examples, leads 162 and 166 can comprise printed traces alongside of or inside of elongate shaft 150. For example, metal ribbons can be printed or otherwise formed on a surface of elongate shaft 150. In yet additional examples, metal traces can be co-extruded with material of elongate shaft 150. In any example, the elongate conducts can be selectively exposed in places during the manufacturing process where sensing is desired to occur, or material of elongate shaft 150 can be removed after the manufacturing process to selectively expose the elongate conducts in a separate step.

Processor 136 can be configured to execute instructions stored in memory 138. Memory 138 can include instruction for processing signals from the positive and negative electrodes. For example, the instructions can include directions for executing the methods illustrated in FIGS. 13-15. Memory 138 can additionally include stored therein threshold, baseline or benchmark levels for the conductivity, impedance, resistance and phase angle of liver, pancreas and a gall bladder that can be compared to signals obtained from electrode 144 and ground 164. Memory 138 can include therein diagnostic information relating to different types of stones that can be formed in duodenum D and common bile duct 124. Memory 138 can further include stored therein identification information for auxiliary scope 134 and biliary diagnostic device 132. Alternatively, biliary diagnostic device 132 can further comprise a separate chip, e.g., a radio frequency identification device (RFID) that can include identifying information, e.g., manufacturer, model, calibration, etc., for auxiliary scope 134 and biliary diagnostic device 132.

Processor 136 can comprise, e.g., a central processing unit (CPU), a graphics processing unit (GPU), a hardware processor core, or any combination thereof. Memory 138 can comprise one or more volatile, non-transitory, or non-volatile tangible computer-readable media. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like. Power source 140 can comprise a generator for producing electric current, such as in the form of low power DC output or low power RF output.

As shown in FIG. 6B, electrode 144 can comprise electrode ring 170 configured to completely encircle lumen 158. In examples, ring 170 can encircle elongate shaft 150. In other examples, ring 170 can be fully or partially embedded within elongate shaft 150. In examples, at least portions of ring 170 are exposed to the exterior of elongate shaft 150 so as to be able to contact tissue or biological material.

As shown in FIG. 6C, electrode 144 can comprise one or more ring segments 172A and 172B that only partially encircle lumen 159. Ring segments 172A and 172B can be positioned on the exterior of elongate shaft 150, partially embedded within elongate shaft 150 or fully embedded within elongate shaft 150. Ring segments 172A and 172B can comprise arc segments, e.g., segments of a circle. FIG. 6C illustrates ring segments 172A and 172B as comprising segments extending over approximately ninety degrees. However, larger or smaller arc segments can be used. Additionally, only one ring segment or more than two ring segments can be used.

Full rings, as shown in FIG. 6A, or a plurality of ring segments that extend around a majority of the perimeter of elongate shaft 150 can be advantageous in increasing sensor input. Ring 170 and ring segments 172A and 172B can comprise metal material suitable for conducting current from power source 140 from leads 162 and 166.

The biliary diagnostic devices of the present disclosure can additionally be configured to perform other procedures. In examples, the biliary diagnostic devices can be configured to perform medical interventions, such as cauterizing. Sensing performed with electrode 144, and other components configured to contact tissue disclosed herein, can be conducted by the application of a voltage between the electrodes, e.g., electrode 144 and ground 164 shown in FIG. 6A. The voltage can be applied by power source 140. Typically, such voltage is fairly low such that only enough current sufficient to generate an electrical signal for sensing is applied. As such, as discussed above, lead 162 need not be provided with additional insulation other than what can be provided by elongate shaft 150. Thus, the conducting components can simply be exposed, such as to contact tissue, to perform sensing. In additional examples, the voltage can be increased to provide cauterizing functionality, e.g., to provide heating of tissue sufficient to stop bleeding, such as by drying out the tissue.

Voltages sufficient for such cauterizing functionality can remain sufficiently low to not require additional insulation and to avoid excess altering of tissue beyond what is needed to cauterize. However, additional insulation can be included in examples. Voltages sufficient for sensing and cauterizing can depend on multiple factors, such as the resistance of tissue that is being sensed. The resistance of the tissue being sensed will depend on the surface areas of the electrodes and the distances the electrodes are apart. For example, power of approximately 10 Watts can affect tissue sufficient to cauterize. The electrode arrangements disclosed herein can have resistances of approximately 250 Ohms or less, though other resistances can occur or be used. As such, the applied voltages can be on the order of 50V or less based on the equation $P=V^2/R$. In examples, sensing without cauterizing can be performed with voltages of approximately 50 Volts or less, while cauterizing can be performed with voltages of approximately 50 Volts or greater. Additionally, an upper limit on the applied voltage, such as 60 Volts, can be set to prevent excess tissue damage. Thus, in an example, sensing can be conducted with voltages in the range of 35-45 volts and cauterizing can be conducted with voltages in the range of 45-55 volts. The values for the ranges listed above are illustrative and other voltages and ranges or combination of ranges may be suitable in other examples and configurations.

FIG. 7 is a perspective view of a second example of a biliary diagnostic device 132 of FIG. 5 with electrode 144 comprising a single electrode ring 170 configured to function as a negative electrode. Biliary diagnostic device 132 of FIG. 7 can be similarly configured as biliary diagnostic device 132 of FIG. 6A, with the exception of lead 166 being connected to guidewire 154 instead of ground 164. Additionally, electrode 144 can be configured as the negative electrode with guidewire 154 being configured as the positive electrode.

FIG. 8 is a perspective view of a third example of biliary diagnostic device 132 of FIG. 5 with electrode 144 and second electrode 180 comprising a pair of electrode rings configured to function as positive and negative electrodes. Biliary diagnostic device 132 of FIG. 8 can be similarly configured as biliary diagnostic device 132 of FIG. 6A, with the exception of lead 166 being connected to electrode 180 instead of ground 164. Additionally, electrode 144 can be configured as the positive electrode with electrode 180 being configured as the positive electrode. Leads 162 and 166 can comprise elongate metal wires that can be joined to electrodes 144 and 180 at distal ends and processor 136 at proximal ends. Processor 136, with input from memory 138, can be configured to determine the conductivity, impedance, resistance and phase angle between electrode 144 and electrode 180.

FIG. 9 is a perspective view of a fourth example of biliary diagnostic device 132 of FIG. 5 comprising electrodes 190 and 192 in addition to electrodes 144 and 180 comprising pairs of electrodes configurable for discrete or combined biliary diagnostic sensing. As shown in FIG. 9, electrode 144 and electrode 190 can be connected to lead 162 and electrode 180 and electrode 192 can be connected to lead 166. Including two electrodes on each of leads 162 and 166 can increase the sensitivity of the single sensor functioning as biliary diagnostic device 132. Leads 162 and 166 can be connected to processor 136 as shown in FIGS. 6A, 7 and 8. In other examples, electrodes 190 and 192 can be provided with separate leads such that biliary diagnostic device 132 can include two separate sensors. As such, with four electrodes functioning as a single sensor, the output of each pair of electrodes, e.g., electrodes 144 and 180 and electrodes 190 and 192, is automatically averaged. However, with four electrodes functioning as dual sensors, the output of each sensor can be averaged by processor 136 or can be weighted as desired. For example, the leading pair of electrodes, e.g., electrodes 144 and 180, can be weighted more heavily than the trailing pair of electrodes, e.g., electrodes 190 and 192, to provide directionality to the output of biliary diagnostic device 132.

The same sensor (e.g., the sensor formed by electrodes 144 and 180 and electrodes 190 and 192) can be used for multiple evaluation checks. Alternatively, individual sensors (e.g., the sensor formed by electrode 144 and 180 and the sensor formed by electrodes 190 and 192) can be used for discrete checks (e.g. one sensor can be used for resistance measurements while another sensor can be used for phase angle). In yet another example, multiple (e.g., all) electrodes can be used for resistance measurements and multiple, other sensors can be used for phase angle. As such, any combination of one or more sensor can be used to sense, conductivity, impedance, resistance and phase angle.

Figure 10:
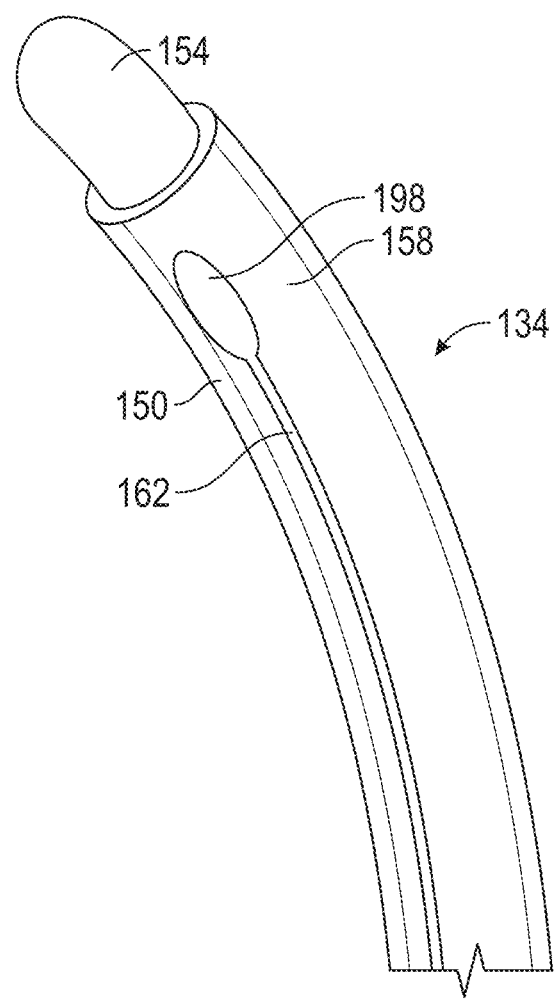
FIG. 10 is a perspective view of a fifth example of a biliary diagnostic device of the present disclosure comprising a single electrode pad configured to function as a positive or negative electrode.

FIG. 10 is a perspective view of a fifth example of biliary diagnostic device 132 of FIG. 5 comprising single electrode pad 198 configured to function as a positive electrode. Biliary diagnostic device 132 of FIG. 10 can be similarly configured as biliary diagnostic device 132 of FIG. 6A or FIG. 7, with the exception of ring electrode 144 being replaced by pad electrode 198. Pad electrode 198 can comprise a flat, thin body that extends about a portion of elongate shaft 150. The surface area of pad electrode 198 can be configured to facilitate interaction with tissue to improve sensitivity of the sensor. For example, pad electrode 198 can be knurled or textured to facilitate engagement with biological matter. In additional examples, pad 198 can be configured as elongate strips extending along a length of elongate shaft 150. Also, although only one pad 198 is illustrated, multiple pads 198 can be included on elongate shaft 150.

FIG. 11 is a schematic view of an output device 142 suitable for use with biliary diagnostic devices 132 disclosed herein. Output device 142 can comprise visual display 200 and audio driver 202. Visual display 200 can comprise output indicia 204A-204E and dial 206. Visual display 200 can comprise an active display unit, such as a liquid crystal display, a plasma screen, an organic light-emitting diode display and the like. Visual display 200 can comprise a touchscreen device. In examples, processor 136 can comprise or be part of control unit 16 of imaging and control system 12 (FIG. 2). As such, visual display 200 can be programmed to provide a variety of outputs and receive a variety of user-inputs.

Activation of at least one of indicia 204A-204E can provide an indication of conductivity, impedance, resistance and phase angle sensed between electrodes of the sensors of biliary diagnostic device 132. With respect to FIG. 5, for example, indicia 204A-204E can be responsive to electrical parameters sensed between electrode 144 and electrode 180. As can be seen in FIG. 5, endoscope 100 can be inserted in duodenum D and auxiliary scope 134 can be positioned for insertion into common bile duct 124. As such, electrode 144 can contact tissue of common bile duct 124, fluids within common bile duct 124 and solids, e.g., stones, within common bile duct 124.

In an example, each of light emitters 204A-204E can be activated to indicate a progressively larger magnitude or level of an electrical parameter. For example, light emitter 204E at the bottom of output device 142 and light emitter 204A at the top of output device 142 can be activated in opposite manners to indicate opposite ends of an electrical property spectrum. For example, light emitter 204E can be activated to show a first level of an electrical property, such as a magnitude of the electrical property just above zero and light emitter 204A can be activated to show a second level of an electrical property, such as a magnitude of the electrical property at a saturation, maximum or threshold level. Light emitters 204B-204D can be activated to indicate varying levels in between the first and second levels such that a continuous spectrum or a gradual changing of light emitting activation can be provided. Light emitters 204A-204E can update in real-time to indicate the magnitude of the electrical parameter. Thus, as a surgeon can manipulate endoscope 100 or auxiliary scope 134 to receive an indication of the type of biological material being engaged by electrode 144.

In other examples, all of light emitters 204A-204E can be activated, or lit up, and can change colors to indicate the magnitude of the electrical parameter.

In an example, visual display 200 can include dial 206. Dial 206 can include a scale to indicate different magnitudes of the electrical parameter and a needle can move to indicate the magnitude being actively sensed. For example, lighter colors can be used to indicates lower conductivity and darker colors can be sued to indicate higher conductivity.

In examples, light emitters 204A-204E and dial 206 can be provided with labels to translate the magnitudes of the sensed electrical parameters into anatomical descriptions. For example, high levels of conductivity can be translated into a liver bile and low levels of conductivity can be translated into pancreatic juice.

In examples, an audible alarm can be used to provide feedback indicating the magnitude of the sensed parameter. For example, a steady signal can be emitted that changes pitch, volume or tone based on the magnitude of the sensed electrical parameter. In other examples, an intermittent signal can be emitted that changes frequency based on the magnitude of the sensed electrical parameter.

FIG. 12A is a perspective view of stent 220 incorporating biliary diagnostic device 222 according to the present disclosure. Stent 220 can comprise tubular body 224, internal lumen 226 and barbs 228. Biliary diagnostic device 222 can comprise electrodes 220A, 220B and 220C. Electrodes 230A-230C can each comprise a sensor configured to sense an electrical parameter of fluid or solid material in tubular body 204. FIG. 12B is a cross sectional view of stent 220 of FIG. 12A taken at section 12B-12B showing electrodes 230A-230B of the biliary diagnostic device 222. FIGS. 12A and 12B are discussed concurrently.

Stent 220 can be positioned within an abdominal passage to strengthen duct tissue or prevent blockage of the abdominal passage. Barbs 228 can be used to anchor or attach tubular body 224 to the abdominal passage. Tubular body 224 can be sized for placement into different sized abdominal passages, such as duodenum D, common bile duct 124 and main pancreatic duct 126 (FIG. 5).

Electrodes 230A-230C can be connected to biliary diagnostic device 132, e.g., at processor 136, (FIG. 6A) via mechanical lead wires. As such, the lead wires can be connected to stent 220 during a procedure or during a check-up of a patient at a medical facility. In other examples, stent 220 can be provided with a wireless communication device, e.g. a radio frequency chip, that can be implanted in the patient with stent 220 such that readings from electrodes 230A-230C can be taken.

FIG. 13 is block diagram illustrating method 300 for performing a chemical analysis using the biliary diagnostic devices of the present disclosure. At step 302, method 300 can be started. For example, endoscope 100 and auxiliary scope 134 can be inserted into duodenum D (FIG. 5). Electrode 144 and any of electrodes 180, 190 and 192 can be positioned into engagement with tissue of duodenum D or any abdominal passaged connecting thereto, such as common bile duct 124 and main pancreatic duct 126. Additionally, biliary diagnostic device 132 can be powered on, such as through power source 140 (FIG. 11) or imaging and control system 12.

At step 304, a sensor of biliary diagnostic device 132 can be activated. For example, electricity from power source 140 can be directed to electrodes 144, 180, 190 and 192. Processor 136 of biliary diagnostic device 132 can be activated based on instructions from memory 138 to read the magnitude of an electrical parameter (conductivity, impedance, phase angel, etc.) between electrode 144 and tissue or another electrode. In the example, of FIG. 13, impedance can be measured with the sensor comprising electrode 144.

At step 306, impedance can be evaluated of the biological material in contact with electrode 144. Processor 136 can compare the sensed impedance against a threshold or baseline impedance X stored in memory 138. Impedance X can be indicative of the presence of liver bile.

If the sensed impedance is greater than X, method 300 can move to step 308. At step 308, output device 142 can be activated by processor 136 to manipulate one or more of visual display 200, audio driver 202 and dial 206 to indicate that biliary diagnostic device 132 sensed a level of impedance indicative of liver bile present in passage 129 (FIG. 5). As such, the surgeon can continue to advance auxiliary scope 134 toward the gall bladder or liver.

If the sensed impedance is less than X, method 300 can move to step 310. At step 310, output device 142 can be activated by processor 136 to manipulate one or more of visual display 200, audio driver 202 and dial 206 to indicate that biliary diagnostic device 132 sensed a level of impedance indicative of a lack of, or a lower concentration of, liver bile as would be present near inlet (ampulla of Vater) 128 (FIG. 5). As such, the surgeon can steer auxiliary scope 134 away from inlet 128 and toward passage 129.

Thereafter, method 300 can return to start 302 or step 304 such that continuous, real-time impedance measurements can be taken.

FIG. 14 is block diagram illustrating method 320 for performing a chemical analysis using biliary diagnostic devices 132 of the present disclosure. Method 320 can comprise steps 302, 304, 306 and 310 as are described with reference to method 300 of FIG. 13. However, instead of step 308, method 320 can comprise step 322 wherein if the sensed impedance is greater than X, method 320 can compare the sensed impedance against a second threshold or baseline impedance Y stored in memory 138. Second impedance Y can be indicative of the presence of different types of stones that can be found in common bile duct 124.

If the sensed impedance is greater than Y, method 320 can move to step 324. At step 324, output device 142 can be activated by processor 136 to manipulate one or more of visual display 200, audio driver 202 and dial 206 to indicate that biliary diagnostic device 132 sensed a level of impedance indicative of a first type of stone in passage 129 (FIG. 5). Furthermore, the surgeon can receive confirmation that the correct route for auxiliary scope 134 has been detected and auxiliary endoscope can be continued to be advanced toward the gall bladder or liver.

If the sensed impedance is less than Y, method 320 can move to step 326. At step 326, output device 142 can be activated by processor 136 to manipulate one or more of visual display 200, audio driver 202 and dial 206 to indicate that biliary diagnostic device 132 sensed a level of impedance indicative of a second type of stone in passage 129 (FIG. 5). Furthermore, the surgeon can receive information that an incorrect route for auxiliary scope 134 has been detected and auxiliary endoscope can be rerouted toward the gall bladder or liver.

Thereafter, method 320 can return to start 302 or step 304 such that repeated impedance measurements can be taken. As such, output of processor 136 can be repeatedly update at short intervals to provide continuous or near real-time impedance measurements to an operator.

FIG. 15 is block diagram illustrating method 340 for performing a chemical analysis using biliary diagnostic devices 132 of the present disclosure. Method 340 can comprise steps 302, 304, 306 and 310 as are described with reference to method 300 of FIG. 13. However, instead of step 308, method 320 can comprise step 342 wherein biliary diagnostic device 132 can sense for phase angle of the biological material in contact with electrode 144. The sensed phase angle can be compared against a threshold or baseline phase angle Z stored in memory 138. Phase angle Z can be indicative of the presence of different types of stones that can be found in common bile duct 124.

If the sensed phase angle is greater than Z, method 340 can move to step 344. At step 344, output device 142 can be activated by processor 136 to manipulate one or more of visual display 200, audio driver 202 and dial 206 to indicate that biliary diagnostic device 132 sensed a level of phase angle indicative of a first type of stone in passage 129 (FIG. 5). Furthermore, the surgeon can receive confirmation that the correct route for auxiliary scope 134 has been detected and auxiliary endoscope can be continued to be advanced toward the gall bladder or liver.

If the sensed phase angle is less than Z, method 340 can move to step 346. At step 346, output device 142 can be activated by processor 136 to manipulate one or more of visual display 200, audio driver 202 and dial 206 to indicate that biliary diagnostic device 132 sensed a level of phase angle indicative of a second type of stone in passage 129 (FIG. 5). Furthermore, the surgeon can receive information that an incorrect route for auxiliary scope 134 has been detected and auxiliary endoscope can be rerouted toward the gall bladder or liver.

Thereafter, method 340 can return to start 302 or step 304 such that continuous, real-time impedance measurements can be taken.

Though methods 300, 320 and 340 have been described with reference to sensing impedance as a primary indicator and phase angle as a secondary indicator, methods 300, 320 and 340 can be operated to sense for any combination of conductivity, impedance, resistance and phase angle. Likewise, though methods 300, 320 and 340 have been described with reference to biliary diagnostic devices and methods for sensing liver bile, other diagnostic processes can conducted, such as diagnosis of pancreas and gall bladder chemical analyses.

VARIOUS NOTES & EXAMPLES

Example 1 can include or use subject matter such as a biliary diagnostic device comprising a tubular body comprising an outer wall, and an internal lumen, and a first biliary diagnostic sensor coupled to the medical device, the first biliary diagnostic sensor comprising a first electrode configured to analyze biological matter in contact with the tubular body.

Example 2 can include, or can optionally be combined with the subject matter of Example 1, to optionally include a first electrode that is configured to determine an electrical property of the biological matter.

Example 3 can include, or can optionally be combined with the subject matter of one or any combination of Examples 1 or 2 to optionally include a first biliary diagnostic sensor that further comprises a lead wire extending from the first electrode, and a power source connected to the lead wire.

Example 4 can include, or can optionally be combined with the subject matter of one or any combination of Examples 1 through 3 to optionally include an output device configured to provide at least one of an audio output and a visual output of an indication of the electrical property.

Example 5 can include, or can optionally be combined with the subject matter of one or any combination of Examples 1 through 4 to optionally include an electrical property that comprises at least one of conductivity, impedance, resistance and phase angle.

Example 6 can include, or can optionally be combined with the subject matter of one or any combination of Examples 1 through 5 to optionally include memory having stored therein a database of electrical properties of liver bile.

Example 7 can include, or can optionally be combined with the subject matter of one or any combination of Examples 1 through 6 to optionally include an identification chip coupled to the biliary diagnostic device containing information relating to a type of a medical device to which the first biliary diagnostic sensor is coupled and calibration of the first biliary diagnostic sensor.

Example 8 can include, or can optionally be combined with the subject matter of one or any combination of Examples 1 through 7 to optionally include a first electrode that comprises a ring circumscribing the internal lumen.

Example 9 can include, or can optionally be combined with the subject matter of one or any combination of Examples 1 through 8 to optionally include a first electrode that comprises a partial ring attachable to the tubular body.

Example 10 can include, or can optionally be combined with the subject matter of one or any combination of Examples 1 through 9 to optionally include a first electrode that comprises a pad attached to the tubular body.

Example 11 can include, or can optionally be combined with the subject matter of one or any combination of Examples 1 through 10 to optionally include a first biliary diagnostic sensor that further comprises a second electrode spaced from the first electrode.

Example 12 can include, or can optionally be combined with the subject matter of one or any combination of Examples 1 through 11 to optionally include a second electrode that comprises a guidewire extending through the internal lumen.

Example 13 can include, or can optionally be combined with the subject matter of one or any combination of Examples 1 through 12 to optionally include a biliary diagnostic device that further comprising a second biliary diagnostic sensor.

Example 14 can include, or can optionally be combined with the subject matter of one or any combination of Examples 1 through 13 to optionally include a second biliary diagnostic sensor that comprises a pair of electrodes electrically coupled and spaced from the first biliary diagnostic sensor along the tubular body.

Example 15 can include, or can optionally be combined with the subject matter of one or any combination of Examples 1 through 14 to optionally include a first biliary diagnostic sensor that comprises a plurality of electrodes.

Example 16 can include, or can optionally be combined with the subject matter of one or any combination of Examples 1 through 15 to optionally include a tubular body that comprises a stent.

Example 17 can include, or can optionally be combined with the subject matter of one or any combination of Examples 1 through 16 to optionally include a tubular body that comprises an endoscope.

Example 18 can include, or can optionally be combined with the subject matter of one or any combination of Examples 1 through 17 to optionally include an endoscope that comprises an elevator.

Example 19 can include, or can optionally be combined with the subject matter of one or any combination of Examples 1 through 18 to optionally include an endoscope that comprises a cholangioscope.

Example 20 can include, or can optionally be combined with the subject matter of one or any combination of Examples 1 through 19 to optionally include an endoscope that comprises at least one of an imaging unit, an illumination unit and a treatment or diagnostic device.

Example 21 can include or use subject matter such as a method of guiding an endoscope to a common bile duct from a duodenum that comprises inserting the endoscope into the duodenum, engaging a sensor of the endoscope with biological matter in the duodenum, electrically analyzing the biological matter with the sensor to identify an electrical parameter, identifying liver bile in the biological matter from the electrical parameter, and guiding the endoscope through the duodenum based on presence of the liver bile.

Example 22 can include, or can optionally be combined with the subject matter of Example 21 to optionally include engaging the sensor of the endoscope with the biological matter by engaging an electrode of the sensor with the biological matter.

Example 23 can include, or can optionally be combined with the subject matter of one or any combination of Examples 21 or 22 to optionally include an electrical parameter that comprises at least one of conductivity, impedance, resistance and phase angle.

Example 24 can include, or can optionally be combined with the subject matter of one or any combination of Examples 21 through 23 to optionally include identifying liver bile in the biological matter by comparing a baseline electrical parameter with the sensed electrical parameter.

Example 25 can include, or can optionally be combined with the subject matter of one or any combination of Examples 21 through 24 to optionally include guiding the endoscope through the duodenum based on presence of the liver bile by guiding a distal tip of the endoscope toward higher concentrations of liver bile.

Example 26 can include, or can optionally be combined with the subject matter of one or any combination of Examples 21 through 25 to optionally include guiding the distal tip of the endoscope toward the liver bile by identifying a sphincter of Oddi in the duodenum.

Example 27 can include, or can optionally be combined with the subject matter of one or any combination of Examples 21 through 26 to optionally include calibrating the sensor by electrically analyzing the duodenum with the sensor to identify the electrical parameter away from the sphincter of Oddi.

Example 28 can include, or can optionally be combined with the subject matter of one or any combination of Examples 21 through 27 to optionally include guiding the distal tip of the endoscope toward the liver bile by identifying an intersection of a main pancreatic duct with the common bile duct.

Example 29 can include, or can optionally be combined with the subject matter of one or any combination of Examples 21 through 28 to optionally include outputting an indicator of the electrical parameter to an operator of the endoscope.

Example 30 can include, or can optionally be combined with the subject matter of one or any combination of Examples 21 through 29 to optionally include analyzing a stone formed in the common bile duct based on the electrical parameter.

Example 31 can include, or can optionally be combined with the subject matter of one or any combination of Examples 21 through 30 to optionally include cauterizing tissue with the biliary diagnostic device.

Example 32 can include or use subject matter such as a method of identifying a composition of biological matter within a bile duct comprising engaging a sensor of a medical device with biological matter in the bile duct, electrically analyzing the biological matter with the sensor to identify an electrical parameter, identifying biological matter from at least one of a liver, pancreas and a gall bladder from the electrical parameter, and outputting an indication of the biological matter to a user of the medical device.

Example 33 can include, or can optionally be combined with the subject matter of Example 32, to optionally include engaging the sensor of the medical device with the biological matter by engaging an electrode of the sensor with the biological matter.

Example 34 can include, or can optionally be combined with the subject matter of one or any combination of Examples 32 or 33 to optionally include an electrical parameter that comprises at least one of conductivity, impedance, resistance and phase angle.

Example 35 can include, or can optionally be combined with the subject matter of one or any combination of Examples 32 through 34 to optionally include identifying the biological matter by comparing a baseline electrical parameter with the sensed electrical parameter.

Example 36 can include, or can optionally be combined with the subject matter of one or any combination of Examples 32 through 35 to optionally include identifying the biological matter by determining a concentration of a fluid comprising the biological matter.

Example 37 can include, or can optionally be combined with the subject matter of one or any combination of Examples 32 through 36 to optionally include a fluid that comprises liver bile.

Example 38 can include, or can optionally be combined with the subject matter of one or any combination of Examples 32 through 37 to optionally include diagnosing a medical condition that leads to stone formation.

Example 39 can include, or can optionally be combined with the subject matter of one or any combination of Examples 32 through 38 to optionally include identifying the biological matter by determining a stone structure comprising the biological matter.

Example 40 can include, or can optionally be combined with the subject matter of one or any combination of Examples 32 through 39 to optionally include a stone structure that comprises at least one of a gall stone and a kidney stone.

Example 41 can include, or can optionally be combined with the subject matter of one or any combination of Examples 32 through 40 to optionally include outputting an indication of the biological matter to a user of the medical device by outputting a visual or an audio indication of a magnitude of the electrical parameter.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "Abut not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A biliary diagnostic system comprising:
   an output device configured to provide at least one of an audio output and a visual output;
   a tubular body extending from a proximal end portion to a distal end portion for insertion into a duodenoscope, the tubular body comprising:
   an outer wall extending between the proximal end portion to the distal end portion; and
   an internal lumen extending at least partially through the tubular body between the proximal end portion and the distal end portion to form a working channel opening to an exterior of the tubular body at the proximal end portion;

non-transitory computer readable medium having stored therein one or more magnitudes of a first parameter for an electrical property of liver bile;

a first biliary diagnostic sensor coupled to the tubular body, the first biliary diagnostic sensor comprising a first electrode configured to analyze biological matter in contact with the tubular body to sense a magnitude of an electrical property of the biological matter and determine presence of liver bile using the first parameter;

wherein the non-transitory computer readable medium further has stored therein instructions executable by a processor to perform a method comprising:

comparing the magnitude of the electrical property sensed with the first biliary diagnostic sensor to the one or more magnitudes of the first parameter for the electrical property of liver bile;

generating a first output signal for the output device indicative of a first type of stone sensed by the first biliary diagnostic sensor if the sensed magnitude of the electrical property is greater than the first parameter, wherein the first output signal causes the output device to activate in a first manner, wherein the first output signal provides an output indicative of the first type of stone, wherein the first type of stone comprises a kidney stone; and generating a second output signal for the output device indicative of a second type of stone sensed by the first biliary diagnostic sensor if the identified electrical property is less than the first parameter, wherein the second output signal causes the output device to activate in a second manner different from the first manner, wherein the second output signal provides an output indicative of the second type of stone, wherein the second type of stone comprises a gall stone; and a first auxiliary device configured to perform a first type of procedure for the first type of stone; and a second auxiliary device configured to perform a second type of procedure for the second type of stone wherein:

the first auxiliary device comprises a forceps; and
the second auxiliary device comprises a sphincterotome.

2. The biliary diagnostic system of claim 1, wherein the first biliary diagnostic sensor further comprises:

a lead wire extending from the first electrode; and
a power source connected to the lead wire.

3. The biliary diagnostic system of claim 2, wherein the output device is configured to provide at least one of an audio output and a visual output of an indication of a proximity of the first biliary diagnostic sensor to liver bile to provide navigation guidance to a main pancreatic duct of a patient.

4. The biliary diagnostic system of claim 3, wherein the electrical property comprises at least one of conductivity, impedance, resistance and phase angle.

5. The biliary diagnostic system of claim 4, wherein the non-transitory computer readable medium has stored therein:

a second parameter for the electrical property of liver bile; and instructions for:

comparing the electrical property sensed with the first biliary diagnostic sensor to the second parameter for the electrical property of liver bile;

generating a third output signal for the output device indicative of the biliary diagnostic system being in proximity to liver bile if the sensed electrical property is greater than the second parameter; and generating a fourth output signal for the output device indicative of the biliary diagnostic system not being in proximity to liver bile if the sensed electrical property is less than the second parameter.

6. The biliary diagnostic system of claim 5, wherein the second parameter comprises an impedance value selected from a database of impedance values for different biological matter and different medical instruments.

7. The biliary diagnostic system of claim 5, wherein the non-transitory computer readable medium has stored therein a database having impedance values for the second parameter for different types of biological matter.

8. The biliary diagnostic system of claim 5, wherein the non-transitory computer readable medium has stored therein a database having phase angle values for the first parameter for different types of stones.

9. The biliary diagnostic system of claim 3, wherein the tubular body comprises an auxiliary scope insertable through the duodenoscope to allow the auxiliary scope to exit a distal end face of the duodenoscope.

10. The biliary diagnostic system of claim 9, further comprising the duodenoscope, wherein the duodenoscope has a working channel and an elevator configured to receive the auxiliary scope.

11. The biliary diagnostic system of claim 10, further comprising a controller comprising the non-transitory computer readable medium and the processor, the controller in communication with the first biliary diagnostic sensor, the controller comprising a controller portion of an imaging and control system of an endoscopy system configured to operate at least one of the duodenoscope and the auxiliary scope.

12. The biliary diagnostic system of claim 9, wherein the auxiliary scope comprises:

a cholangioscope and the internal lumen comprises an open working channel configured to receive a treatment or diagnostic device; and at least one of an imaging unit, an illumination unit and a treatment or diagnostic device.

13. The biliary diagnostic system of claim 1, further comprising an identification chip coupled to the biliary diagnostic system configured to contain information related to a type of a medical device to which the first biliary diagnostic sensor is coupled and information related to calibration of the first biliary diagnostic sensor.

14. The biliary diagnostic system of claim 1, further comprising a second electrode, wherein the second electrode comprises a guidewire extending through the internal lumen and protruding from the tubular body.

15. The biliary diagnostic system of claim 1, wherein the biliary diagnostic system further comprises a second biliary diagnostic sensor.

16. The biliary diagnostic system of claim 15, wherein the second biliary diagnostic sensor comprises a pair of electrodes electrically coupled and spaced from the first biliary diagnostic sensor along the tubular body.

17. The biliary diagnostic system of claim 1, wherein the first biliary diagnostic sensor comprises a plurality of electrodes.

18. The biliary diagnostic system of claim 1, wherein the first output signal and the second output signal comprise electrical signals.

19. The biliary diagnostic system of claim 18, wherein the output device comprises:
an audio driver configured to generate the audio output in response to the first output signal and the second output signal; and
a visual display configured to generate the visual output in response to the first output signal and the second output signal.

20. The biliary diagnostic system of claim 1, wherein the non-transitory computer readable medium has instructions stored therein executable by the processor to record the type of stone sensed before the stone is destroyed.

21. The biliary diagnostic system of claim 1, wherein the non-transitory computer readable medium has instructions stored therein executable by the processor to identify the first auxiliary device connected to the biliary diagnostic system to perform the first type of procedure or the second auxiliary device connected to the biliary diagnostic system to perform the second type of procedure.

22. A biliary diagnostic device comprising:
an endoscope comprising:
a tubular body extending from a proximal end portion to a distal end portion, the tubular body comprising:
an outer wall extending between the proximal end portion to the distal end portion; and
an internal lumen extending at least partially through the tubular body between the proximal end portion and the distal end portion to form a working channel opening to an exterior of the tubular body at the proximal end portion;
a camera module mounted to the distal end portion of the tubular body and configured to generate an imaging signal;
an illumination unit mounted to the distal end portion of the tubular body and configured to emit light;
a first biliary diagnostic sensor coupled to the tubular body, the first biliary diagnostic sensor comprising a first electrode configured to analyze biological matter in contact with the tubular body by sensing a magnitude of an electrical property of the biological matter; and
non-transitory computer readable medium having stored therein:
one or more magnitudes of a first parameter for an electrical property of liver bile;
wherein the non-transitory computer readable medium further has stored therein instructions executable by a processor to perform a method comprising:
comparing the magnitude of the electrical property sensed with the first biliary diagnostic sensor to the one or more magnitudes of the first parameter for the electrical property of liver bile;
generating a first output signal for an output device indicative of a first type of stone sensed by the first biliary diagnostic sensor if the sensed magnitude of the electrical property is greater than the first parameter, wherein the first output signal causes the output device to activate in a first manner;
generating a second output signal for the output device indicative of a second type of stone sensed by the first biliary diagnostic sensor if the sensed magnitude of the electrical property is less than the first parameter, wherein the second output signal causes the output device to activate in a second manner different from the first manner; and
adjusting a magnitude of an applied voltage to the first electrode after the first type of stone or the second type of stone has been sensed;
wherein adjusting the magnitude of applied voltage to the first electrode after the first type of stone or the second type of stone has been identified comprises adjusting the applied voltage from a first, lower voltage adequate for performing sensing to a second, higher voltage adequate for performing an anatomic intervention; and
wherein the anatomic intervention comprises cauterizing of tissue.

23. The biliary diagnostic device of claim 22, wherein the first electrode comprises a portion of a lead wire where a coating has been removed to expose the lead wire.

24. The biliary diagnostic device of claim 22, wherein the first electrode comprises a metal ribbon printed on an exterior of the tubular body.

25. The biliary diagnostic device of claim 22, wherein adjusting the magnitude of applied voltage to the first electrode after the first type of stone or the second type of stone has been sensed further comprises turning off the applied voltage.

* * * * *